(12) United States Patent  (10) Patent No.: US 8,701,998 B2
Vollmer et al.  (45) Date of Patent: Apr. 22, 2014

(54) SYSTEM AND METHOD FOR STRONG PHOTON LOCALIZATION BY DISORDERED PHOTONIC CRYSTAL STRUCTURES

(75) Inventors: Frank Vollmer, Cambridge, MA (US); Juraj Topolancik, Malden, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 451 days.

(21) Appl. No.: 12/602,677

(22) PCT Filed: Jun. 4, 2008

(86) PCT No.: PCT/US2008/065745
§ 371 (c)(1),
(2), (4) Date: Dec. 2, 2009

(87) PCT Pub. No.: WO2008/151224
PCT Pub. Date: Dec. 11, 2008

(65) Prior Publication Data
US 2010/0176200 A1  Jul. 15, 2010

Related U.S. Application Data

(60) Provisional application No. 60/941,950, filed on Jun. 4, 2007, provisional application No. 60/980,816, filed on Oct. 18, 2007.

(51) Int. Cl.
*G06K 7/10* (2006.01)

(52) U.S. Cl.
USPC ............ 235/454; 235/462.15; 235/462.1; 385/131

(58) Field of Classification Search
USPC .............. 235/454, 462.15, 462.1; 385/131
See application file for complete search history.

(56) References Cited

U.S. PATENT DOCUMENTS

| 6,917,431 | B2 | 7/2005 | Soljacic et al. | |
|---|---|---|---|---|
| 7,289,221 | B2 | 10/2007 | Wang et al. | |
| 7,307,732 | B2 | 12/2007 | Beaudoleil | |
| 7,446,880 | B2 | 11/2008 | Vollmer et al. | |
| 7,471,866 | B2 | 12/2008 | Dumais et al. | |
| 7,492,979 | B2 | 2/2009 | Wang et al. | |
| 2002/0150366 | A1* | 10/2002 | Loncar et al. | 385/125 |
| 2004/0062505 | A1* | 4/2004 | Sugitatsu et al. | 385/131 |
| 2005/0110992 | A1* | 5/2005 | Scherer et al. | 356/318 |
| 2006/0024013 | A1 | 2/2006 | Magnusson et al. | |
| 2006/0066866 | A1 | 3/2006 | Wang et al. | |
| 2006/0140567 | A1 | 6/2006 | Kittaka et al. | |
| 2009/0136181 | A1 | 5/2009 | Vollmer et al. | |
| 2009/0237666 | A1 | 9/2009 | Vollmer et al. | |

FOREIGN PATENT DOCUMENTS

WO  2006108096  10/2006

* cited by examiner

*Primary Examiner* — Sonji Johnson
(74) *Attorney, Agent, or Firm* — 24IP Law Group; Timothy R DeWitt

(57) ABSTRACT

Periodic high-index-contrast photonic crystal (PhC) structures such as two-dimensional arrays of air holes in dielectric slabs inhibit light propagation in bands of frequencies and confine light in dislocations where the lattice periodicity is broken. The present invention is a conceptually different approach to photon localization in PhC structures. The disclosed design concept introduces structural perturbations uniformly throughout the fabricated crystal by deliberately changing the shape or orientations of elements that form the lattice. Optimized introduction of such random structural perturbations produces optical nanocavities with ultra-small modal volumes and high quality (Q) factors of over 250,000. Applications of such disordered photonic crystal structures are disclosed for optical sensing systems and random nanolasers.

17 Claims, 20 Drawing Sheets

US 8,701,998 B2

SYSTEM AND METHOD FOR STRONG PHOTON LOCALIZATION BY DISORDERED PHOTONIC CRYSTAL STRUCTURES

CROSS-REFERENCE TO RELATED APPLICATIONS

The present invention claims the benefit of the filing dates of U.S. Provisional Patent Application Ser. No. 60/941,950, entitled "Devices and Methods Based on Strong Photon Localization in Disordered Photonic Crystal Waveguides" and filed on Jun. 4, 2007 and U.S. Provisional Patent Application Ser. No. 60/980,816, entitled "Disorder-Induced High-Q Cavities in Photonic Crystal Structures" and filed on Oct. 18, 2007.

The above cross-referenced related applications are hereby incorporated by reference herein in their entirety.

STATEMENT REGARDING FEDERALLY SPONSORED RESEARCH OR DEVELOPMENT

None.

BACKGROUND OF THE INVENTION

Field of the Invention

Optical cavities defined in periodic high-index-contrast structures which exhibit photonic bandgap (PBG) can localize light by Bragg-scattering in record-low modal volumes of less than cubic wavelength while preserving Quality (Q-) factors ~1 million. Such photonic crystal (PhC) cavities find various applications as optical sensing systems and low-threshold lasers. Any new confinement mechanism in PhC is therefore technologically relevant since new architectures for passive and active photonic devices can be realized. To this end, it was predicted that multiple scattering by random impurities in a disordered lattice can severely impede and even halt diffusion of electromagnetic waves, providing a new mechanism for light localization besides conventional Bragg-scattering. The theory of disorder-induced localization was originally developed for electrons in atomic crystals, but can be extended to electromagnetic (and other) wave phenomena. Strong (Anderson) localization at optical frequencies, however, was successfully demonstrated in only a few experiments that utilized highly-scattering random media. Although it has been proposed that Anderson localization should be possible to attain in disordered PBG structures, no PhC structures that exhibit such spectral signatures have been reported.

The present application discloses designs and design files for PhC structures in which random departures from perfect index-periodicity produce a fundamentally different type of coherent localization analogous to that observed in strongly-scattering random media. Strong localization in randomized PhC structures can find various applications, which we disclose for random lasers and optical sensing systems.

SUMMARY OF THE INVENTION

Periodic high-index-contrast photonic crystal (PhC) structures such as two-dimensional arrays of nanometer-sized air holes in dielectric slabs confine light in defects where the lattice periodicity is broken. Localized optical modes are formed in cavities that are defined by removing, shifting or changing the size of the lattice components. Optimized introduction of such local structural perturbations has produced optical nanocavities with ultra-small modal volumes (less than a cubic wavelength) and high quality (Q) factors of over a million. The present invention is a conceptually different approach to photon localization in PhC structures. The present invention introduces structural perturbations uniformly throughout the fabricated crystal by deliberately changing the shape of lattice elements (typically void regions), referred to as "elements," that form the PhC. Such nanometer-scale disorder effectively represents randomly-distributed strong scatterers that affect propagation of Bloch-waves through the otherwise periodic lattice of the quasicrystal. We disclose design files for disordered PhC waveguides which experience coherent backscattering that leads to Anderson localization. The effect is observed in a narrow frequency band close to the guided mode's cutoff where the light propagates with a slow group velocity (slow light regime) and interaction with the superimposed disorder is strongest. Optical cavities with Qs of $\sim 2 \times 10^5$ and micron-scale modal volumes are observed along disordered waveguides. The present invention can find various applications which we disclose for optical sensing systems and self-optimized random nano-lasers.

In a preferred embodiment, the present invention is an optical device comprising a slab, wherein the slab comprises a material, and a plurality of elements (or void regions) arranged in a lattice. The lattice elements are formed in the slab by removing slab material. Each lattice element has a center located at a position (x,y), wherein first and second lattice elements differ in shape depending on their position (x,y) in the lattice. In one embodiment, a fill-factor (fractional area) of lattice elements, spacing of lattice elements and symmetry/arrangement of lattice elements is chosen so that the device exhibits one or more photonic band gaps. The slab may comprise a composite material that may comprise layers of different materials. The layers of material may comprise, for example, GaAs substrate, AlGaAs, GaAs with self assembled InGaAs quantum dots. In other embodiments, the slab material may comprise a material selected from the group of: silicon, doped silicon, n or p-doped silicon, semiconductor material, colloidal quantum dots, epitaxially grown quantum dots, InGaAs, GaAs, InGaAsP, III-V materials, erbium doped silicon, erbium doped silica, ytterbium doped silicon, ytterbium doped silica, silica, positive photoresist, negative photoresist. In still another embodiment, lattice elements may be removed at lattice positions (x,y) so that a row of missing elements is formed along a crystallographic direction of the lattice. The different shapes of lattice elements may be, for example, circular shapes where a function r defining the radius is parameterized by an angle alpha, r(alpha), and where r(alpha) is not a constant. The function defining the circular shape r(alpha) may be a random function. In other embodiments, the lattice elements comprise polygons or ellipses, and orientations of said polygons or ellipses is varied throughout the lattice, for example, by rotating a given polygon by an angle defined by a function alpha (x,y) that varies with lattice position (x,y) of the polygon within the xy-lattice of elements. The function alpha(x,y) that defines the orientation angle alpha of said polygon at said lattice position (x,y) may be a function that exhibits a certain distribution of values for alpha and may be random.

In a preferred embodiment, the present invention is a photonic crystal-based waveguide that gives rise to spectral features which bear signatures of Anderson localization. Further, it is an apparatus for excitation of disordered photonic crystal waveguides in the slow-light regime using non-linear optical fiber taper as well as provisions and methods needed for collecting transmission and scattering spectra.

In still other embodiments, the optical device may be modified by removing a certain number of said lattice elements at certain lattice positions (x,y). The removed lattice elements may define, for example, a defect cavity, an add-drop filter, a Mach-Zehnder interferometer, and a waveguide. The optical device may be fabricated using jitter of a patterning ebeam to vary said shape of elements throughout said lattice.

In still another embodiment, one of the slab materials comprises an optical gain medium selected from the group of quantum dots, Erbium, Ytterbium, and colloidal quantum dots. Quantum dots are grown in one or more layers using molecular beam epitaxy. In another embodiment one of the materials is deposited on the slab that defines the lattice In another embodiment of this invention, the random quasi-modes in a disorderd photonic crystal waveguide are used to create a random laser. For this purpose it is necessary to introduce a photoluminescent source such as Quantum wells (QWs) or quantum dots (QDs) or any other gain medium in the photonic crystal slab. The gain medium such as quantum wells or quantum dots can be either embedded in the slab forming a heterostructure, or, for the case of quantum dots, placed on the surface of the patterned materials. These photoluminescent sources can be pumped optically or electrically. Optical pumping can be achieved through the non-linear optical fiber taper coupled to the disordered waveguide or by focusing the pump beam onto a spot on the disordered waveguide. Electrical pumping is in principle possible by fabricating metal contacts directly on the surface of the photonic crystal slab.

In another embodiment, a tapered optical fiber tip is used to couple light to one or more lattice positions (x,y) where said lattice elements have been removed. In another embodiment, one or more of the slab materials is emitting light. The emission of light may show gain-induced narrowing of linewidth (laser) or show characteristics of light amplified stimulated emission of radiation (laser).

In another embodiment, the lattice of elements is fabricated using photolithography. The photolithography may be with a limited resolution of the smallest (circular) feature that can be optically defined.

In another embodiment, The difference in shape of said lattice elements is defined by a disorder function of permittivity $\epsilon_{real}(r)$ so that $\Delta\epsilon(r)=\epsilon_{real}(r)-\epsilon_{ideal}(r)$, where $\epsilon_{ideal}(r)$ represents the permittivity of the unperturbed lattice (with perfect translational symmetry) at position of vector r and $\Delta\epsilon(r)$ represents disorder introduced as a variation of that permittivity.

In another embodiment, the present invention is a method for coupling to photonic crystal waveguides in the slow-light regimes that uses an optical fiber tip fabricated by tapering of a single mode optical fiber in a hot flame, cutting of the tapered region after the mid section and further etching in hydrofluoric acid until the mid section separates and leaves a sharp fiber tip.

In another embodiment of this invention, disordered photonic crystal slabs are used as sensors. The frequency of the waveguide bandedge (mode cutoff), and therefore the location of the random quasimodes, is shifted by perturbations to the photonic crystal slab such as: 1) refractive index variations of silicon slab induced by temperature changes; 2) variation of the refractive index of the surrounding medium by exposure to fluids or gases. 3) Binding of molecules to the PhC surface at locations of the quasimodes which leads to polarization of the bound molecule at optical frequency which changes the energy of the exciting quasimode. The change of energy is measured as shift of the frequency (wavelength) for the exciting localized mode.

In one embodiment, an adlayer of molecules is directly deposited on a surface or mode volume of the disordered photonic crystal waveguide. This may be achieved by exposing the structure to a liquid with dissolved molecules e.g. in a microfluidic channel. The specific binding of molecules to a surface or mode volume can be achieved by modification of the surface or the volume with a ligand. For example, an antibody may be adsorbed directly to the PhC surface, which may be silicon.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIG. 16(a) is a schematic diagram of the active cavity characterization scheme.

FIG. 16(b) is a graph of emission spectra of a silicon random photonic crystal microcavity with PbSe quantum dots measured at 300K at different pump powers.

FIG. 16 (d) emission peak linewidth versus pump powers of a silicon random photonic crystal microcavity with PbSe quantum dots measured at 300K at different pump powers.

DETAILED DESCRIPTION OF THE PREFERRED EMBODIMENTS

Figure 1:
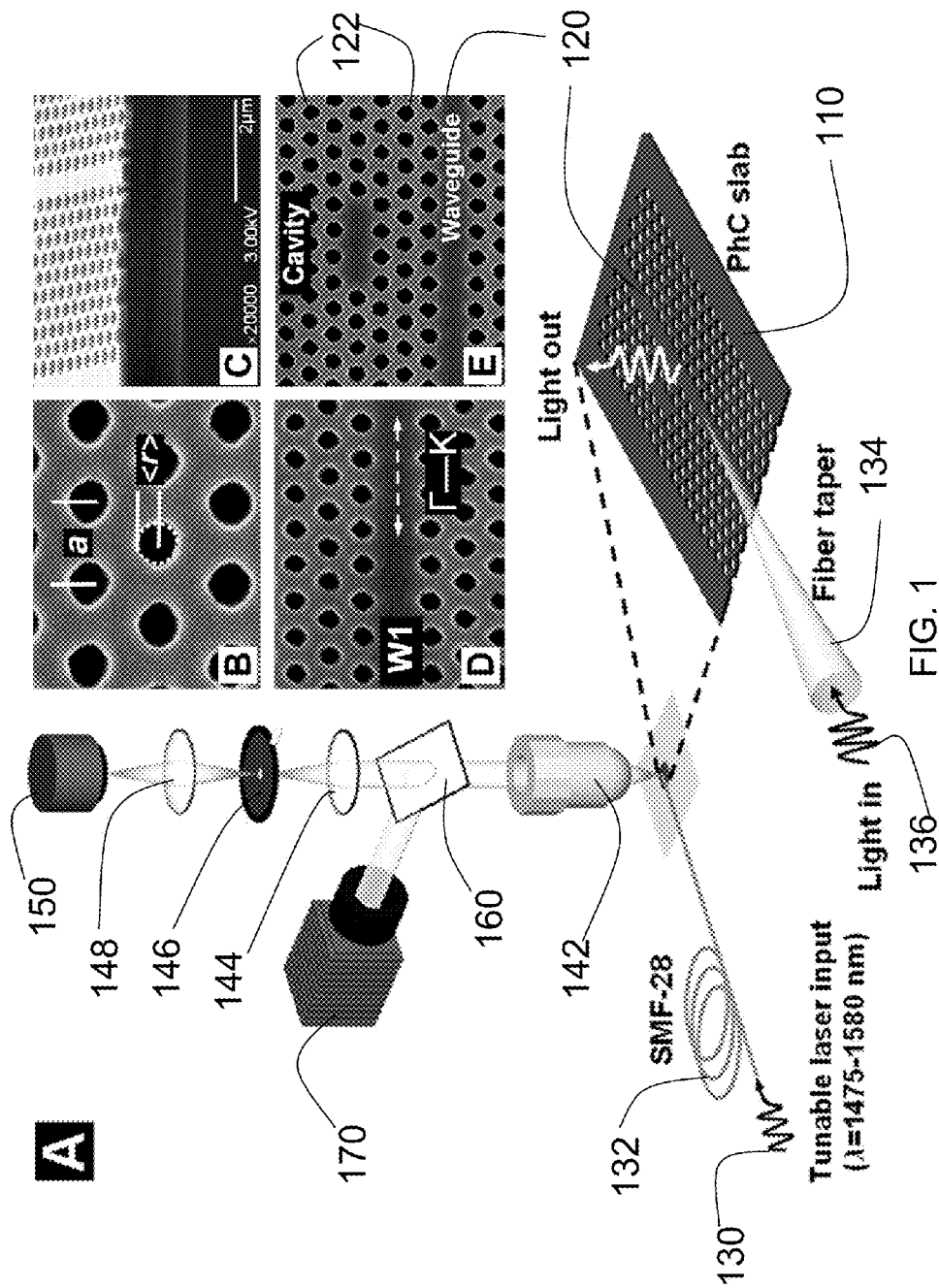
FIG. 1A is a schematic of the measurement setup used in a preferred embodiment.
FIG. 1B is an SEM of a typical disordered PhC lattice where shape of the air-holes is randomized. Notice that the shape differs noticeably from that of a perfect circle (~6 nm superimposed radial variations).
FIG. 1C is a cross-section of a free-standing disordered W1 PhC waveguide.
FIG. 1D is a top image of a W1 waveguide.
FIG. 1E is an example of a donor-defect cavity separated from the waveguide by three rows of holes.

As shown in FIG. 1A, disordered PhC structures consisting of a hexagonal lattice of holes were patterned in silicon-oninsulator substrates using electron beam lithography and chlorine-based inductively coupled plasma reactive ion etching. PhCs 110 with various fill factors (f=⟨⟨/α, where ⟩⟩ is the effective hole radius and a is the lattice constant, as shown in FIG. 1B, were fabricated. As illustrated in the scanning electron micrograph (SEM) in FIG. 1B, the fabricated patterns carry a significant geometrical disorder in addition to the usual surface roughness caused by fabrication. The air-holes form an array with a lattice constant α=410 nm; their size (Area=π⟨ ⟩$^2$) is fairly constant with a standard deviation of 3.6%; but their shape deviates noticeably from an ideal circle. More explicitly, the roundedness (or circularity) of the holes, defined as $4\pi \times$Area/Perimeter$^2$, is 0.85 whereas values very close to unity are readily achieved with state-of-the-art lithographic tools. The introduced geometrical perturbations are small enough not to significantly affect the band structure of the underlying periodic lattice (this way the traditional PBG defect engineering concepts such as bandgap, point-defect mode, line-defect dispersion, etc. still apply), but sufficient to generate significant multiple-scattering of Bloch-waves necessary for strong localization. Once the holes were etched into the ~210-nm-thick silicon layer, the patterns were cleaved and the buried oxide layer was removed with a buffered hydrofluoric acid solution forming a free-standing PhC slab shown in FIG. 1C. The inner walls of the etched holes are smooth and nearly vertical. The disordered PhC enfolds a ~60-μm-long line-defect waveguide (W1) 120 formed by a row of missing holes along the ΓK direction of the reciprocal-lattice, surrounded on both sides by ten rows of holes 122 (see FIGS. 1C and D). Various donor-defect cavities defined by a single or multiple missing holes were also patterned in some samples near the waveguides. An example of a linear, three-defect cavity is shown in FIG. 1E.

Coherent light from an infrared (IR) diode laser 130 tunable from 1,475 to 1,580 nm, was coupled into W1s from a single-mode optical fiber (SMF-28) 132. To compensate for the significant impedance mismatch inherent to conventional end-fire coupling, PhC modes were excited with a non-linear fiber taper 134. The taper, prepared by pulling a melted fiber and etching its tip down to the W1 dimensions ($\sqrt{3} \times \alpha$), was positioned on top of the PhC-slab 110 as illustrated in FIG. 1A.

Vertically scattered light from a photonic crystal slab (PhC) 110 is collected with an objective 142 and imaged with a lens 144 onto a field-stop 146 consisting of a variable aperture which restricts analysis of scattered light to a certain area on the PhC slab. Another lens 148 re-focuses light from the selected area into an IR photodiode 150. A beam splitter 160 redirects a fraction of the collimated beam into an IR charge coupled device camera 170 for imaging. The arrangement allows the light 136 to leak out of the taper 134 and to evanescently couple into W1 120. Once excited, the PhC modes propagate in the waveguide 120 and interact with cavities which leak the light vertically out of the slab. This light was collected with an infinity-corrected objective 142 (100×, NA=0.80) and its intensity monitored with an InGaAs photodiode 150 as the coherent source 130 was scanned. A beam-splitter 160 redirected a fraction of the collimated beam to an IR camera 170 for imaging. A field stop 146 was placed in front of the photodiode 150 to locally probe 10 μm-long waveguide sections and to block parts of the free-propagating beam deflected accidentally into the objective from surface impurities.

Figure 2:
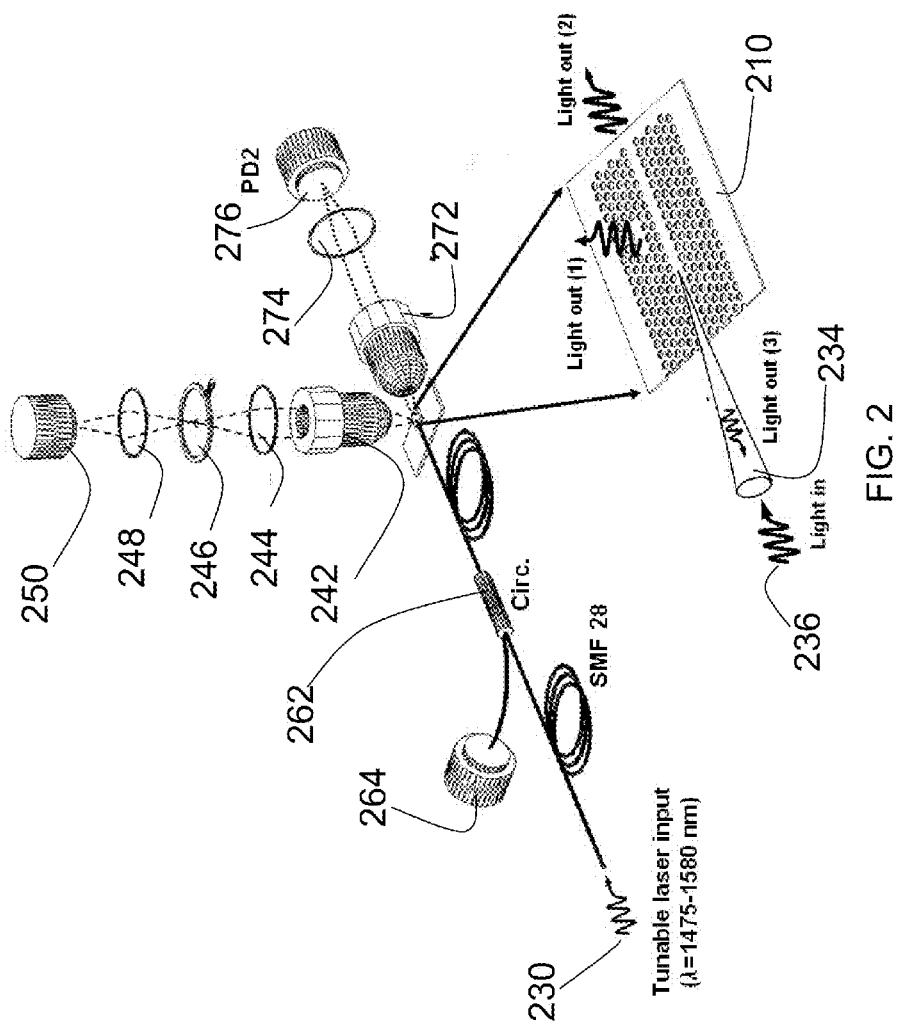
FIG. 2 illustrates three possible configurations to collect a scattering/transmission spectrum from the PhC waveguide.

FIG. 2 illustrates a modification of this basic setup that allows for measurements of transmission spectra (FIG. 2 light out (2)), as well as for measurements of backscattering spectra (FIG. 2, light out (3)). The first configuration relies on an objective 242 that collects light scattered vertically from the PhC waveguide (Light out 1). A lens 244 focuses the light onto a field stop 246 which is used to restrict the analysis of scattered light to a local (~10 μm spot) region on the waveguide. After refocusing through another lens 248 the light is detected by photodetector 250. The second configuration relies on backscattering from the PhC waveguide using an optical circulator 262 or waveguide coupler. The nonlinear-fiber taper 234 is then used to excite resonances and collect (Light out 3) light from localized modes. The circulator reroutes the backscattered signal onto photodetector 264. The third configuration relies on a second objective 272 to collect the light transmitted through the disordered PhC waveguide (Light out 2), through a lens 274 and onto a photodiode 276. The localized modes then appear as transmission dips. Similar may be achieved by collecting the light with a second non-linear optical fiber taper that is aligned at the output of the waveguide. Transmission spectrum can then be recorded with a fiber-coupled photodetector.

Figure 3:
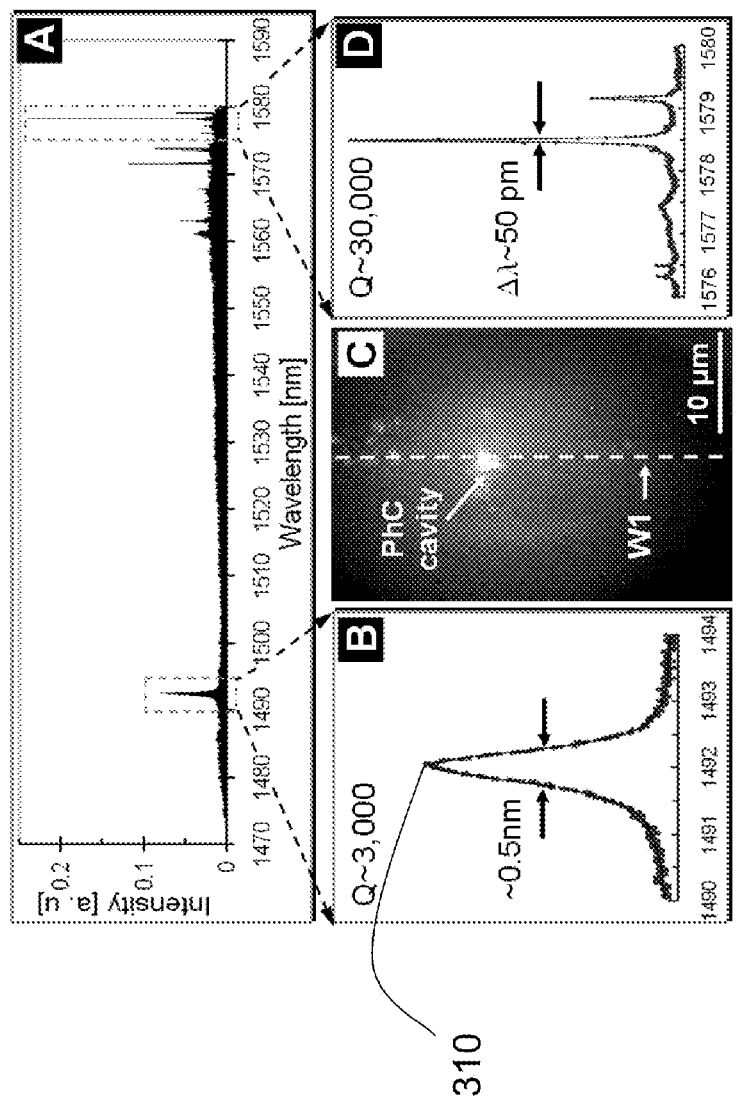
FIG. 3A is a spectrum acquired from a disordered W1 waveguide with additional defect cavity. The structure is shown in FIG. 1E.
FIG. 3B is a 4 nm-wide detailed scan showing the solitary broad feature attributed to the defect cavity.
FIG. 3C is an IR image of the PhC slab.
FIG. 3D is a high-resolution scan of a 4 nm-wide section of the band containing sharp spectral peaks.
Figure 4:
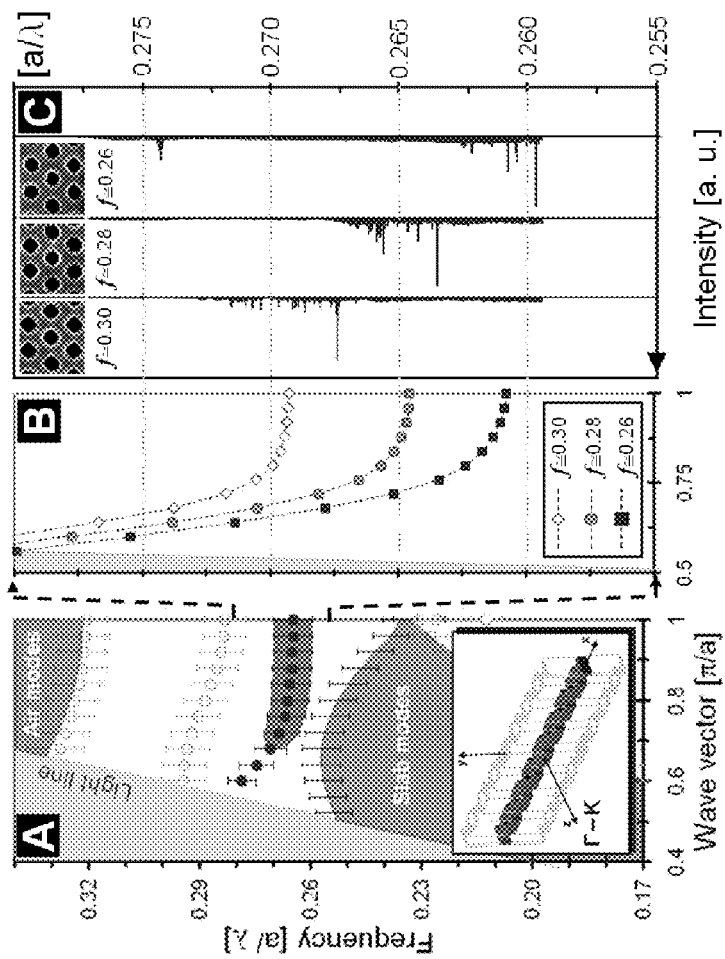
FIG. 4A is a calculated band structure of a W1 waveguide (f≅0.28) with an even-parity guided-mode (black circles). The dark-shaded region around the mode's edge outlines the strong-localization window. The inset shows the supercell used in the plane-wave expansion simulations.
FIG. 4B is a calculated dispersion curves for the even mode in waveguides with three different fill factors.
FIG. 4C is a spectra collected from fabricated waveguides with the equivalent fill factors. The insets show the corresponding SEM images of the PhC structures.

The spectrum collected from a donor-defect cavity separated from W1 by four rows of holes is shown in FIG. 3A. It contains two distinct features: an isolated peak 310 at 1,492 nm with the Q of ~3,000 (FIG. 3B), as inferred from its full width at half maximum linewidth; and a striking series of extremely sharp ($\Delta\lambda \sim 50$ pm), discrete peaks in a narrow band centered at ~1,570 nm (FIG. 3D). The IR image in FIG. 3C indicates that the analyzed light is emitted primarily from the donor-cavity region. To explain the origins of the measured spectra we need to address the dispersion characteristics of PhC waveguides and describe how they are affected by disorder. Although it is possible to systematically study how specific types of disorder affect transport through waveguides, e.g. by analyzing ensembles of randomized structures with the finite-difference-time-domain (FDTD) method, this would require unreasonably large simulation domains and unfeasible computation times. Instead, here we use the established supercell approach and 3D plane-wave expansion to calculate band structure of line-defects in ideal, disorder-free crystals; and qualitatively explain how disorder affects dispersion and gives rise to the observed spectral features. R. D. Meade et al., "Accurate theoretical analysis of photonic band-gap materials," Phys. Rev. B 48, 8434 (1993). The supercell used to compute the band diagrams is shown in the inset of FIG. 4A. Its dimensions are $7\sqrt{3}\alpha \times 4\alpha \times \alpha$ and the refractive index of silicon used in the simulations is n=3.52. S. Adachi, "Model dielectric constants of Si and Ge," Phys. Rev. B 38, 12966 (1988). The simulated slab is ~0.51×α-thick and the holes are circular with radii that correspond to the fill factors of the fabricated PhCs which were determined from the analysis of SEM images. FIG. 3(a) shows the projected band-structure of a W1 with f≅0.28. To conceptually show the effect of disorder we introduce error bars representing uncertainty in the computed eigenfrequencies. Their magnitude in FIG. 4A is arbitrary and is merely meant to reflect the severity of disorder, i.e., how much the departures from holes' circularity affect the eigenvalue uncertainty. A single non-leaky mode bounded by the light-line ($\omega \cong 0.283[\alpha/\lambda]$) and the stop-band ($\omega \cong 0.265[\alpha/\lambda]$) falls within the scan-range of the probing laser. The mode has an even parity and exhibits anomalous dispersion unique to PhC waveguides. Its group velocity ($v_g = d\omega/dk$) gradually decreases as the wave-vector approaches the zone boundary (the slow-light regime). We attribute the solitary spectral peak at 1,492 nm ($\omega \cong 0.2748[\alpha/\lambda]$) to a point-defect cavity mode excited evanescently by the waveguide in the classical (or index-guided) regime. Even though the crystal disorder reduces the PBG and degrades the cavity Q, it permits proper waveguiding and Bragg localization. Whereas the isolated resonance can be accounted for with the conventional donor-cavity PBG defect picture, the sharp peaks at longer wavelengths (in the slow-light regime) cannot be explained within the simple framework. Instead, we contend that these features are caused by disorder and are a manifestation of Anderson localization.

Figure 5:
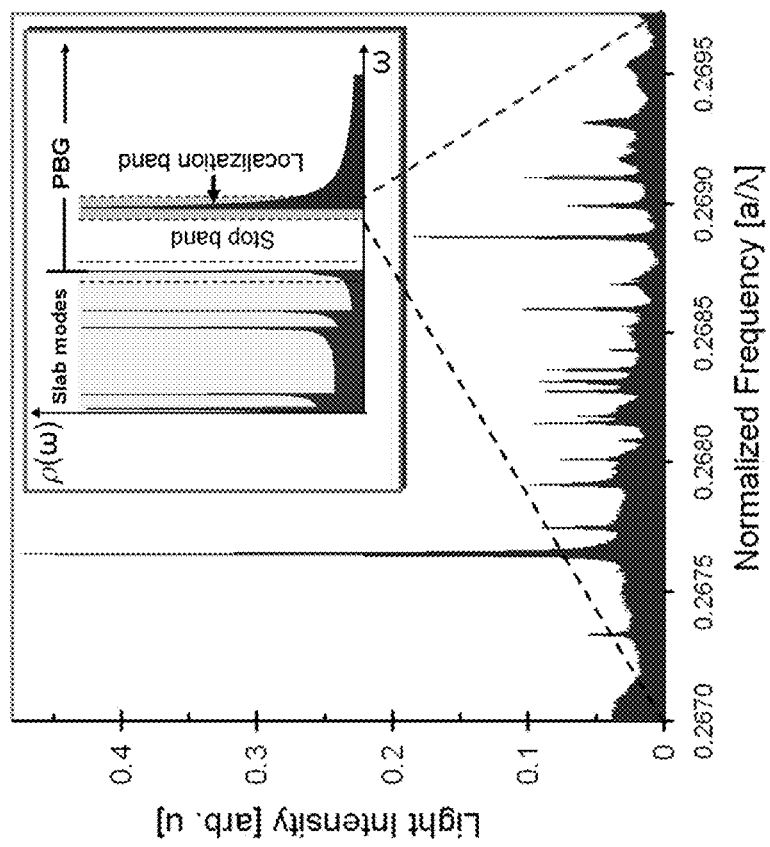
FIG. 5 is a detailed spectrum collected from a disordered W1 (f≅0.30). The inset shows the calculated density of states (DOS) of a defect-free waveguide. Disorder creates a localization band (gray) around the slow-mode's cutoff.

Calculated dispersion diagrams of even modes in W1 waveguides with different fill factors: f=0.26, f=0.28 and f=0.30 are presented in FIG. 4B. The plots indicate that increasing f shifts the mode's edge to higher frequencies. The same trend is observed experimentally for the bands of narrow peaks measured on the fabricated disordered waveguides with equivalent fs (FIG. 4C), which suggests that the spectral position of the spectral feature is dictated by the band structure. Our measurements directly probe the spectral characteristics of local fields in the PhC structure by analyzing the light scattered vertically by donor-cavities. The cavities are usually off-resonance in the bandwidth where the peaks are present and they merely enhance the scattering efficiency out of the PhC slab. Distinct Bragg defect-modes, such as the one shown in FIG. 3B, are seldom detected. This is because their spectral positions and Qs depend sensitively on the cavity-geometry and disorder generally either degrades the Q or shifts the resonant frequency outside the limited scan-range of the probing laser. On the other hand, pronounced narrow spectral features always appear, even in disordered waveguides fabricated without donor-cavities. In this case the sharp peaks are observed, though with a reduced intensity, in arbitrary locations along the probed waveguides. A close-up of the spectrum collected from a section of a disordered W1 with no donor-cavity (f≅0.30) is presented in FIG. 5. The scan reveals a band with multiple sharp resonances, rather than a broad spectral feature anticipated as a result of the increased vertical-scattering loss from the waveguide in the slow-light regime. S. Hughes et al., "Extrinsic Optical Scattering Loss in Photonic Crystal Waveguides Role of Fabrication Disorder and Photon Group Velocity," Phys. Rev. Lett., 94, 033903 (2005). The highly-coherent character of the detected light suggests that the introduced geometrical disorder changes the nature of scattering in this narrow band: diffusive scattering due to surface roughness is suppressed, being dominated by coherent scattering that leads to localization. As a result, a localization window, outlined as a dark-shaded area around the mode's edge in FIG. 4A, opens in the k-ω space. The physical origins of strong localization in disordered W1s can be explained within the context of theories of wave propagation in disordered media. A. F. Ioffe and A. R. Regel, Prog. Semicond. 4, 237 (1960); D. J. Thouless, "Maximum Metallic Resistance in Thin Wires," Phys. Rev. Lett. 39, 1167 (1977); Y. A. Vlasov, M. A. Kaliteevski, and V. V. Nikolaev, "Different regimes of light localization in a disordered photonic crystal," Phys. Rev. B. 60, 1555 (1999).

It can be argued that introduction of random disorder fills the edge of the stop-band with quasistates creating a string of resonant cavities along the waveguide. The defect states that populate the stop-band are well-localized, i.e. spatially and spectrally distinct, only if their level spacing ($\Delta v$) is large enough and the level width ($\delta v$) are small enough so that the modes do not overlap. This essentially says that another fundamental localization condition, the Thouless criterion ($\delta \equiv \delta v/\Delta v < 1$), is satisfied. Significantly-overlapping modes would enable transport and destroy localization. The origin of the localization band is shown schematically in the inset of FIG. 5. A disorder-free W1 exhibits an abrupt transition from the guided mode to the stop-band, i.e. the density-of-states (DOS) of the guided modes, $\rho(\omega) \propto (v_g)^-$, diverges at the mode's cutoff beyond which it suddenly vanishes. Disorder causes band-structure fluctuations that smear the sharp cutoff creating a transitional (or impurity) band filled with both, slowly-guided modes credited to the residual refractive-index periodicity and localized quasistates arising from disorder. Light-propagation in the band can be viewed as a combination of remnant waveguiding and resonant transport. The observed localized quasimodes with effective Qs of over 30,000 (FIG. 5) are in many respects similar to engineered defect-modes in PhC-heterostructure cavities in which periodicity of PhC waveguides is broken intentionally by locally increasing the lattice constant. These modes have small modal volumes and record-high Qs of up to $\sim 10^6$.

Figure 6:
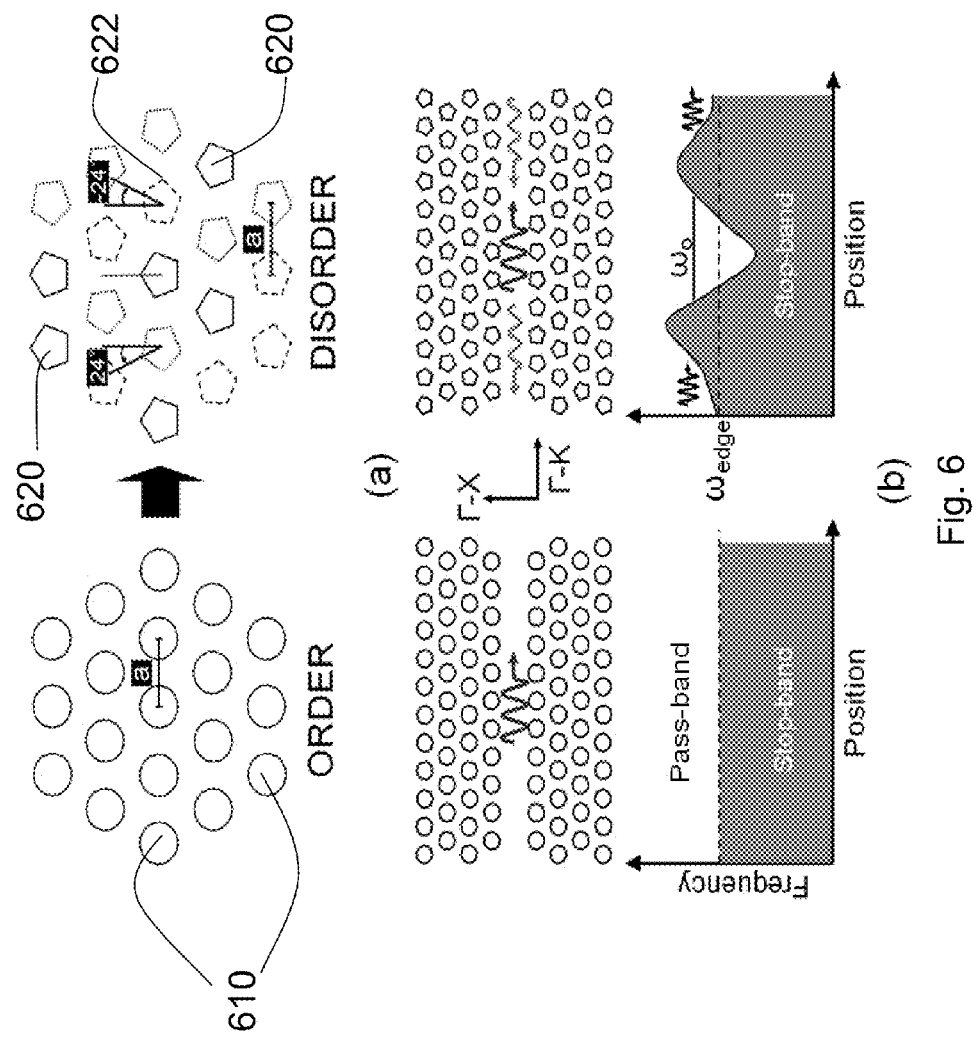
FIG. 6(a) is a description of an introduced lattice disorder in a preferred embodiment. Circular lattice elements, i.e., void regions, in the hexagonal array are replaced with pentagon lattice elements with three specified orientations.
FIG. 6(b) is a schematic illustration of the effect of disorder on the band structure of Γ-K line-defect waveguides (left: ideal structure with no superimposed disorder, right: structure that is disordered due to randomized orientation of polygonal lattice elements). Top: an extended propagating wave (black) is back-scattered (gray) by disorder which results in its localization in the disordered case (right). Bottom: an alternative localization picture. Fluctuations of the stop-band edge ($\omega_{edge}$) create wells in which photons of certain energies ($\omega_0$) are confined in the disordered case (right).

In another design, as shown in FIG. 6A, the average PhC periodicity is preserved while replacing conventional circular patterns 610 in the design files with randomly oriented polygons. This simple realization of disorder is different from the one described before where shape perturbations of the lattice elements was achieved by applying random deflection jitter to the patterning electron beam (EB). The previous approach lacked analytic control over the superimposed roughness-function and did not allow systematic introduction of long-range correlations for future studies of wave transport and localization. In the present invention the PhC platform is composed of a hexagonal array of pentagons 620, some of which 622 are rotated around their centers by 24° in the clockwise or the anticlockwise direction as shown in FIG. 6A. The design files for patterning of the photonic crystal structure may be created, for example, with AutoCad (or similar) software. The design files are then converted to an appropriate file format that is then used to steer the patterning electron beam. The orientation of the pentagon at a particular lattice point is chosen at random while the total numbers of features with a specific orientation are equal. The lattice constant a=410 nm and the average air-fill-factor of ~30% are fixed throughout the PhC. The disorder introduced in this way goes beyond the usual surface roughness caused during fabrication, but the underlying lattice periodicity is mostly preserved. Single-line-defect waveguides (W1s) were defined in the hexagonal array by removing rows of pentagons along the Γ-K lattice symmetry direction. W1 s formed in disorder-free PhCs composed of circular holes are known to exhibit a stop-band (or mode-gap), which is a band of frequencies where wave transport is prohibited. TE-polarized electromagnetic (EM) waves (electric field parallel to the crystal plane) are guided in the pass-band of these structures by the photonic bandgap within the PhC plane and by total internal reflections in the out-of-plane direction. Introduction of disorder perturbs the translational symmetry of the waveguide causing slight fluctuations of the stop-band boundary which effectively creates opaque barriers through which EM waves evanescently couple into transparent wells in which they become confined. This is illustrated schematically in FIG. 6B where a cavity with a resonant frequency is formed in the proximity of the unperturbed mode-edge ($\omega_{edge}$) by disorder-induced backscattering of the propagating wave. Tuning of the barrier heights and well dimensions by design is an established way of photon localization by the so-called mode-gap effect which has been employed extensively to engineer high-Q nanocavities with ultra-small modal volumes. See B.-K. Song, S. Noda, T. Asano, and Y. Akahane, Nature 4, 207 (2005) and A. Kuramochi, M. Notomi, S. Mitsugi, A. Shinya, and T. Tanabe, Appl. Phys. Lett. 88, 041112 (2006). The system at hand can be essentially regarded as an experimental realization of mode-gap confinement in randomized PhCs. While sharing the conceptual origin, random resonators are different from designed nanocavities in the following way. Geometry of an engineered cavity is usually optimized with a systematic parametric search aimed to reduce the modal volumes and minimize losses. The cavity resonances are excited evanescently from a feeding waveguide and their Qs are dictated by the strength of the in-plane coupling to the waveguide and vertical coupling to the continuum. On the other hand, a cavity in a disordered W1 is excited by resonant tunneling through other cavities along the waveguide which form a chain of coupled random open resonators. The coupling process is a research topic in itself as it leads to interesting wave transport and localization phenomena. See P. Sebbah, B. Hu, J. M. Klosner, and A. Z. Genack, Phys. Rev. Lett. 96, 183902 (2006) and J. Bertolotti, S. Gottardo, and D. S. Wiersma, Phys. Rev. Lett. 94, 113903 (2005). The Q of a cavity in the random chain depends on its geometry and the strength of lateral coupling to its neighbors and the fabrication-induced surface roughness which causes additional scattering. It is conceivable that disordered structures support low-loss cavity geometries which have so far not been discovered by parametric optimization. Deliberate introduction of random disorder could therefore further improve Qs of PhC-based nanocavities. Theoretical investigations of one-dimensional systems with various levels of disorder suggest that there is an optimum amount of defects which maximizes the quality of confinement. See S.-H. Chang, H. Cao, and S. T. Ho, IEEE J. Quantum Electron 39, 364, (2003). These results therefore suggest that cavities in partially ordered structures (that exhibit PBG) should have Q-factors superior to those supported by completely random systems. See V. Milner and A. Z. Genack, Phys. Rev. Lett. 94, 073901-1 (2005).

Figure 7:
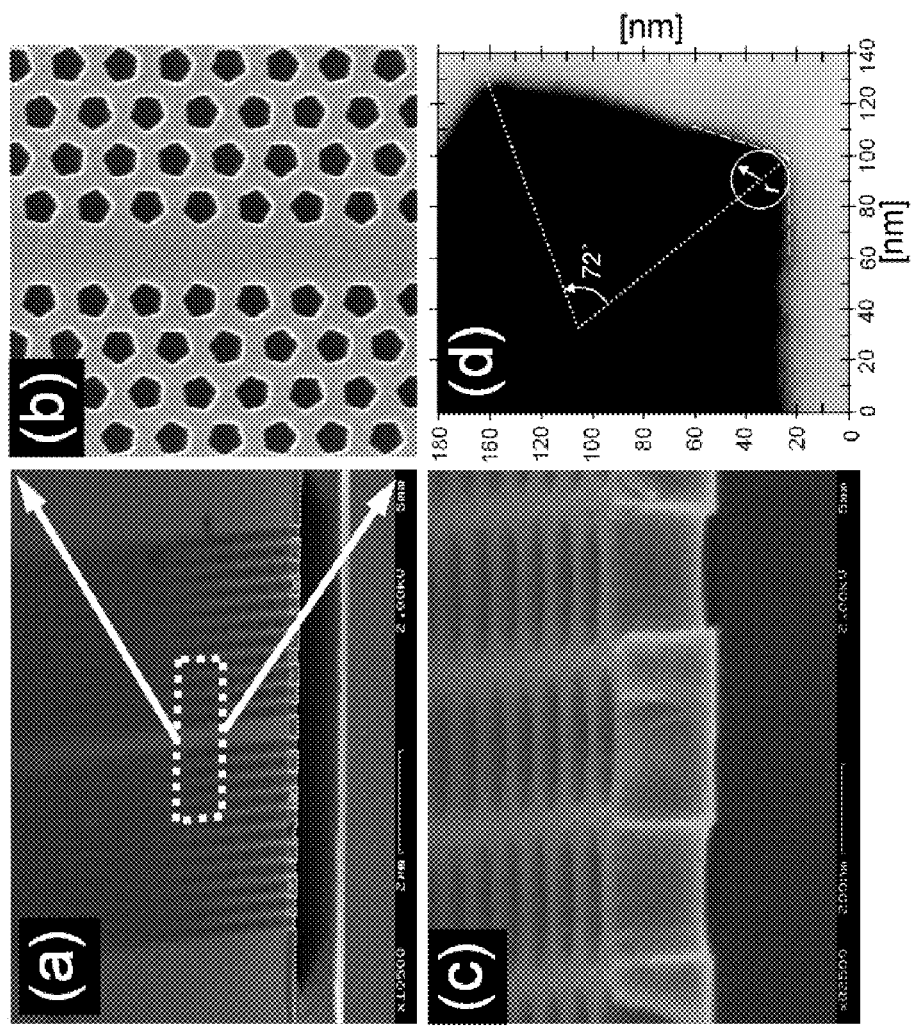
FIG. 7(a) is a SEM image of the fabricated PhC slab.
FIG. 7(b) is a top view of the randomized pattern.
FIG. 7(c) is a detailed micrograph of the cleaved facet showing the tilt and the surface roughness of the etched wall.
FIG. 7(d) is an atomic force microscope (AFM) image showing the top edge roughness and the rounded vertices of a pentagonal air-hole.

The disordered PhCs were fabricated on silicon-on-insulator (SOI) substrates using EB lithography and two-step reactive ion etching (RIE). The SOI wafers were first thermally oxidized to form a 220 nm-thick Si layer clad by 30 nm of thermal oxide from above and 1 μm of buried oxide (BOX) from below. The polynomial patterns were then defined with a 100 kV EB (JEOL 9300) and transferred into the top oxide layer with the first RIE step based on $CHF_3/O_2$ chemistry. The thermal oxide layer was then used in the second RIE step as a hard mask to etch through Si with inductively-coupled $Cl_2/BCl_3/H_2$ plasma. The BOX layer and the residual thermal oxide were eventually removed with buffered hydrofluoric acid forming 220 nm-thick free-standing PhC slabs. The fabricated pentagons have rounded vertices with a curvature of r≅10 nm; the etched sidewalls are vertical within 4° from the plane normal; and the fabrication-induced surface roughness is <5 nm as determined from scanning electron (SEM) and atomic force micrographs (AFM) of the processed structures shown in FIG. 7.

Figure 8:
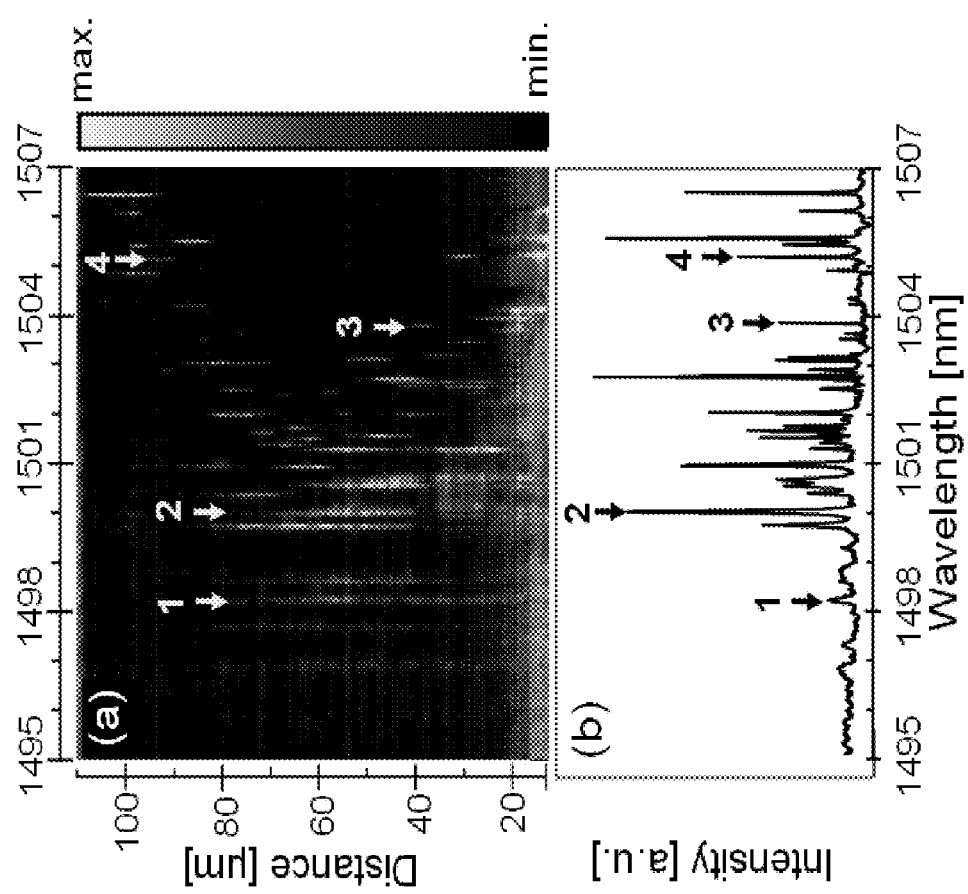
FIG. 8(a) is a contour plot of spatially-resolved spectra of the vertically-dissipated light from a 110 μm-long disordered waveguide. Line-scans are imaged along the waveguide for several wavelengths in the localization band, here 1495 nm-1507 nm. Wavelength-scan step-size is 5 pm. Spatial positions up to ~13 μm from the edge are not shown due to excessive surface-scattering in that region.
FIG. 8(b) illustrates a total, spatially-integrated spectra of the same sample showing multiple Lorentzian-shaped resonances.

TE-polarized output of a tunable infrared diode laser ($\lambda$=1, 475-1,580 nm, 100 kHz linewidth, 2 pm tuning resolution) was coupled evanescently into the disordered W1s from an adiabatic taper prepared from a single-mode telecom fiber. The fiber taper was prepared by pulling a single mode SMF-28 fiber heated by a nitrous-oxide/butane flame. The 1 cm long taper was then cut after the mid-section. The fiber taper region was then immersed in a 50% hydrofluoric acid solution and etched until the mid section (thinnest section) of the taper region is completely dissolved. The so produced fiber tip is ~0.5 cm long, mechanically stable, and tapers from 125 μm single-mode fiber diameter down to less than 1 μm tip diameter. The sharp tip provides a distribution of k-vectors necessary to excite photonic crystal waveguides in the slow light regime at efficiencies much higher as compared to continuous fiber tapers. See P. E. Barclay, K. Srinivasan, M. Borselli, and O. Painter, Electron. Lett. 39, 842 (2003). The light leaking vertically out of the PhC waveguide was collected with an infinity-corrected 100× objective (NA=0.80). The intensities and spatial profiles of the collected radiation patterns were monitored with an InGaAs camera (Sensors Unlimited, SU320MX-1.7RT) while the wavelength of the coherent laser was scanned. A LABVIEW program was used to generate 2D intensity maps of the spatially-resolved spectra which match the spectral features with the positions of sources of the detected light. FIG. 8(a) shows the contour plot acquired from a typical, 110 μm-long disordered W1. The x axis is the wavelength of the collected light and the y axis is the distance from the edge of the waveguide. The spectral component of the displayed data shows a ~10 nm-broad band filled with multiple pronounced peaks with effective Qs ranging from several thousands to ~150,000. The Qs were estimated from the full width at half-maximum of the Lorentzian-shaped peaks shown in the spatially integrated spectra in FIG. 8(b). The contour plot shows that the vertically-leaking light is emitted from "hot spots" of various sizes which are distributed randomly along the disordered waveguide. The observed resonances are localized in waveguide sections ranging from less than 2 μm to a significant fraction of the waveguide length. Although the size and the shape of the observed emission patterns could not be determined more precisely due to the limited resolution of our imaging system, the captured images are sufficient to conclude that the disordered W1 contains nanocavities with sub-wavelengt-cubed modal volumes.

Figure 9:
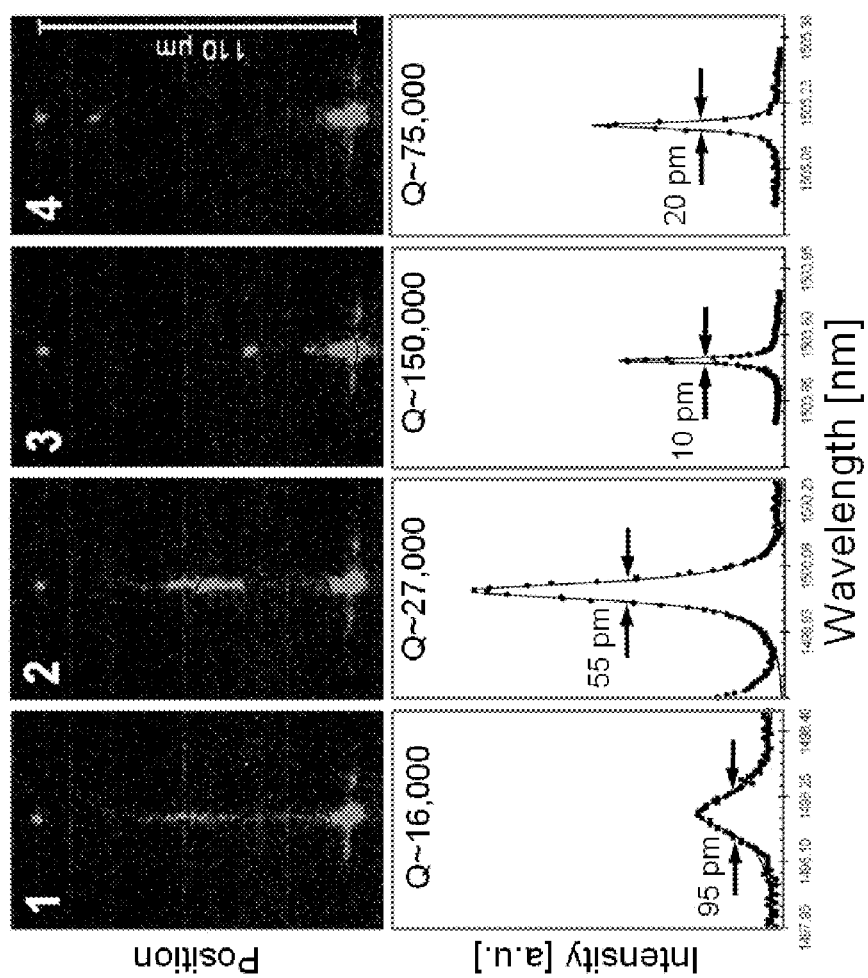
FIG. 9 is a group of near infra-red images of the scattered fields (top) and detailed spectra (bottom) for four wavelengths marked in FIG. 8(a). The localized modes are indicated by circles. The light is incident from the bottom and the bright spot that marks the end of the waveguide and is present at all scanned wavelengths is caused by scattered light reflected to the waveguide's outlet from the other facet of the ~3 mm-long cleaved sample.

Detailed scans of spectrally isolated modes of various Qs and localization lengths, together with images of their field distributions on resonance, are presented in FIG. 9. Resonance 1 extends far into the waveguide and contains several spatially separated intensity peaks. It has a relatively low Q and can be explained with a series of coupled resonators. Resonance 2 is a textbook example of an exponentially localized wave in a random medium with the maximum field intensity at the center of the sample 15. Resonances 3 and 4 are especially interesting as they are extremely-well localized deeply in the waveguide and exhibit high Q factors. We would like to note that the effective Q of ~150,000 (Resonance 3) is less than an order of magnitude smaller that the record-high value measured in PhC cavities (Q~1,200,000) See T. Asano, B.-S. Song, and S. Noda, Opt. Express 14, 1996 (2006). Having compared spatially-resolved spectra of W1s with different realizations of disorder we conclude that the quality of confinement improves with increasing excitation wavelength, i.e. the localization lengths shrink and the Qs rise as the spectral penetration into the stop-band of the underlying periodic system increases.

Figure 10:
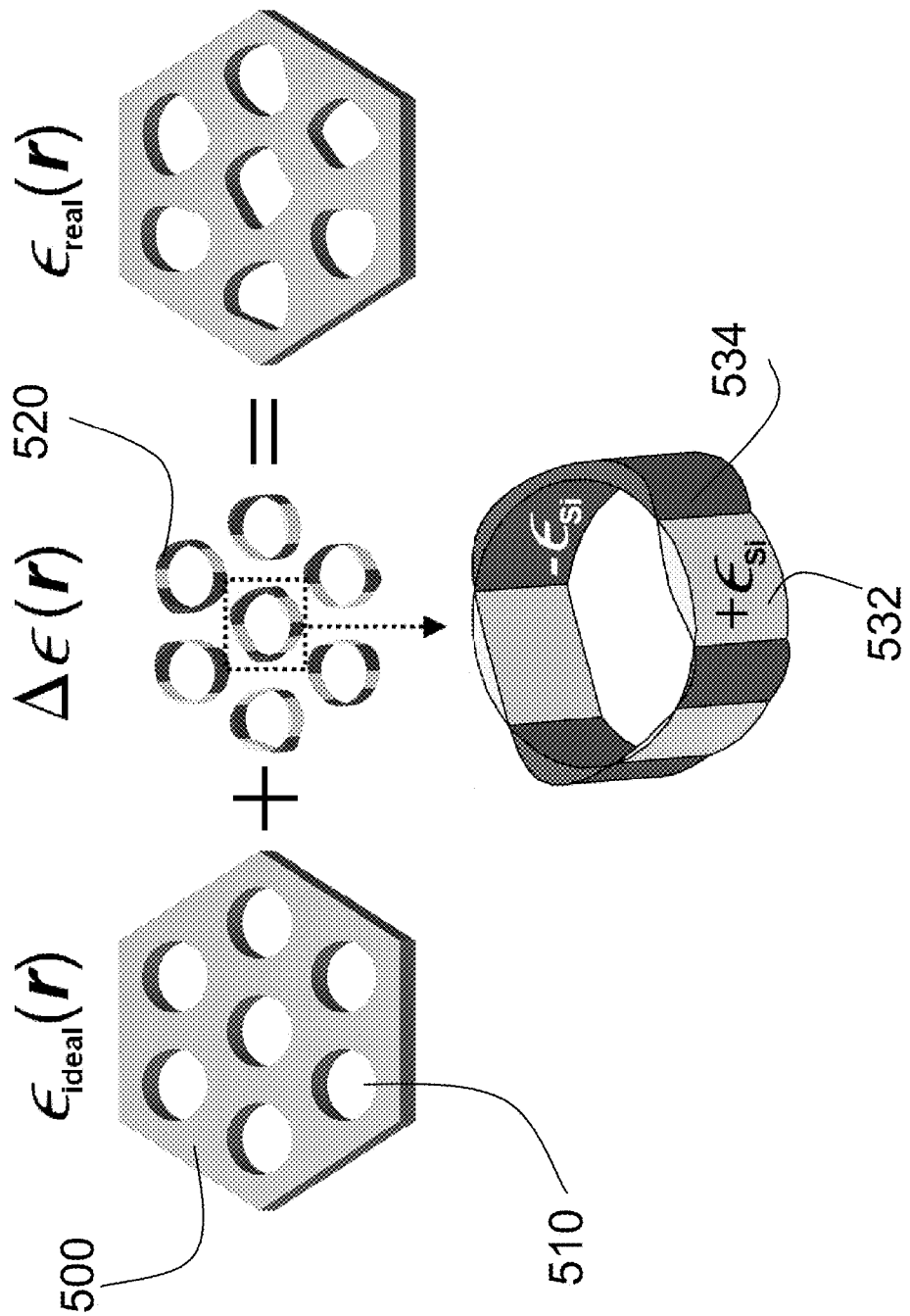
FIG. 10 is a schematic representation of a disorder function $\Delta\epsilon(r)$.

In further preferred embodiments, various imperfections in a two-dimensional PhC lattice of air holes in free-standing silicon slabs were investigated. The air-holes 510 were arranged in a hexagonal array with a lattice constant a such that r/a~0.28 and h/a=0.55, where r is the hole radius and h is the slab thickness. The PhC structures were fabricated on silicon-on-insulator substrates using electron-beam lithography and reactive ion etching. The random scatterers 520 can be represented by a disorder function $\Delta\epsilon(r)$ defined as the difference between the ideal periodic structure $\epsilon_{real}(r)$ (hexagonal array of circular air-holes) and the real disordered structure $\epsilon_{real}(r)$, i.e. $\Delta\epsilon(r)=\epsilon_{real}(r)-\epsilon_{ideal}(r)$. The disorder function can be visualized as columns of materials 532, 534 with positive- and negative permittivities as shown schematically in FIG. 10.

Figure 11:
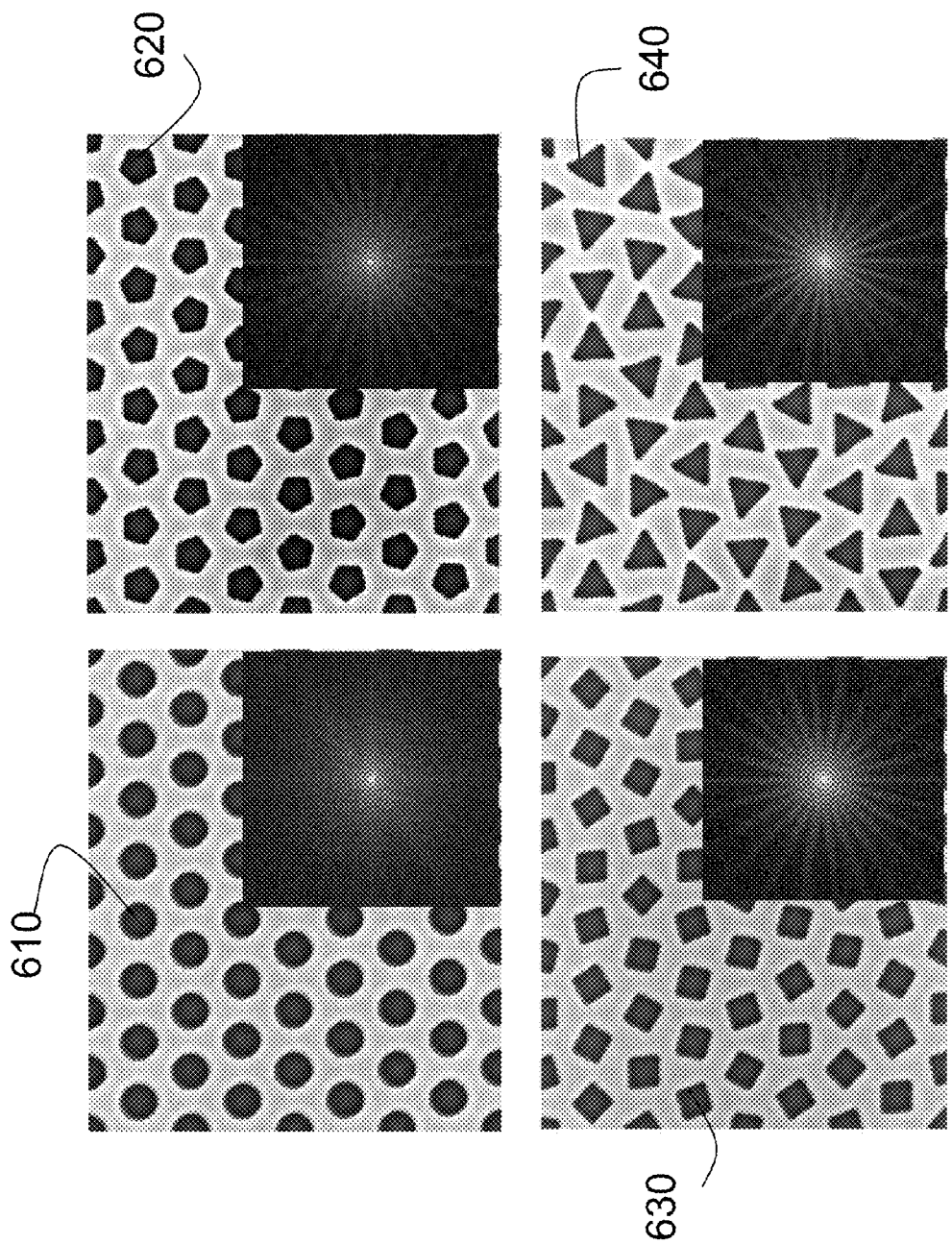
FIG. 11 is a group of SEM images of various realizations of disorder with the corresponding Fourier image transforms investigated in some embodiments.

To cause more severe disorder in a systematic and controlled way the circular patterns 610 in the individual design files were replaced with higher-order polygons, viz. pentagons 620, squares 630, and triangles 640, as shown in FIG. 11, and the translation symmetry of the PhC lattice was broken by randomly varying orientations of the lattice elements. All the polygons in the design files have their surface areas equal to that of a circle in the perfect lattice; the orientation of the feature at a particular lattice point is chosen at random and the total numbers of features with a specific orientation are equal. Micrographs of the fabricated PhC platforms with various scattering strengths and the corresponding Fourier image transforms are shown in FIG. 11.

Figure 12B:
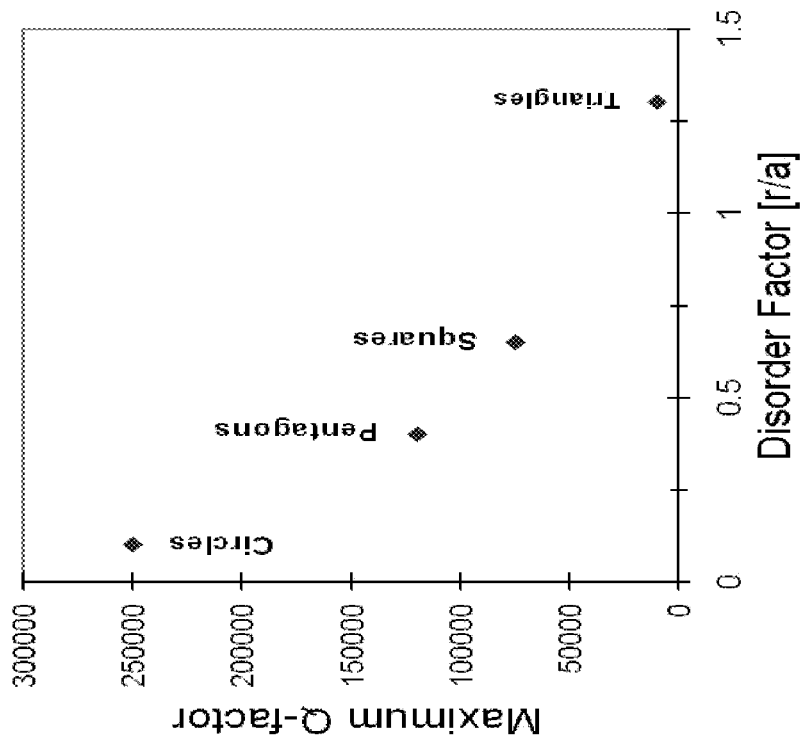
FIG. 12(b) corresponding maximum recorded Q-factors.
Figure 12A:
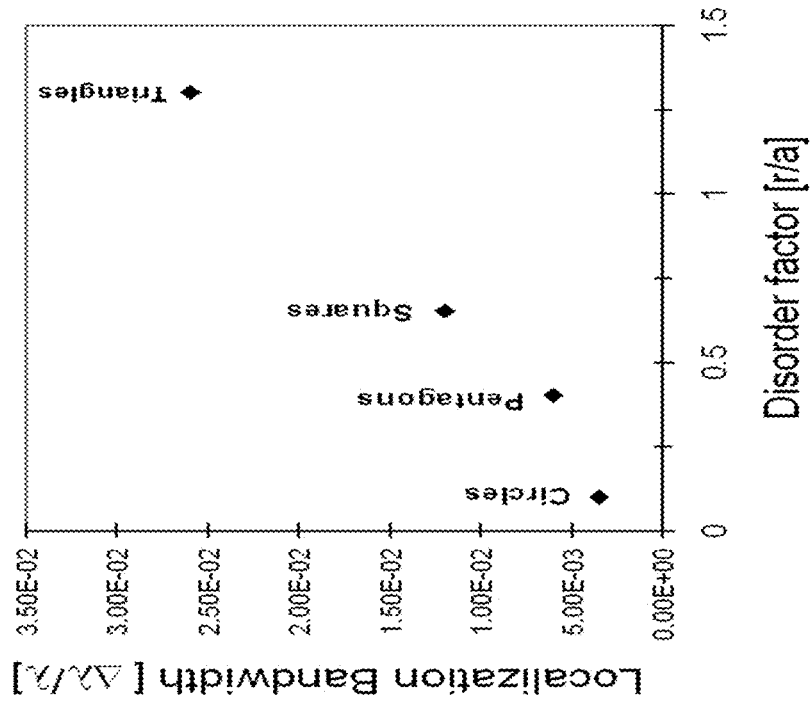
FIG. 12(a) is a plot of the localization bandwidth for four types of disorder.
Figure 13:
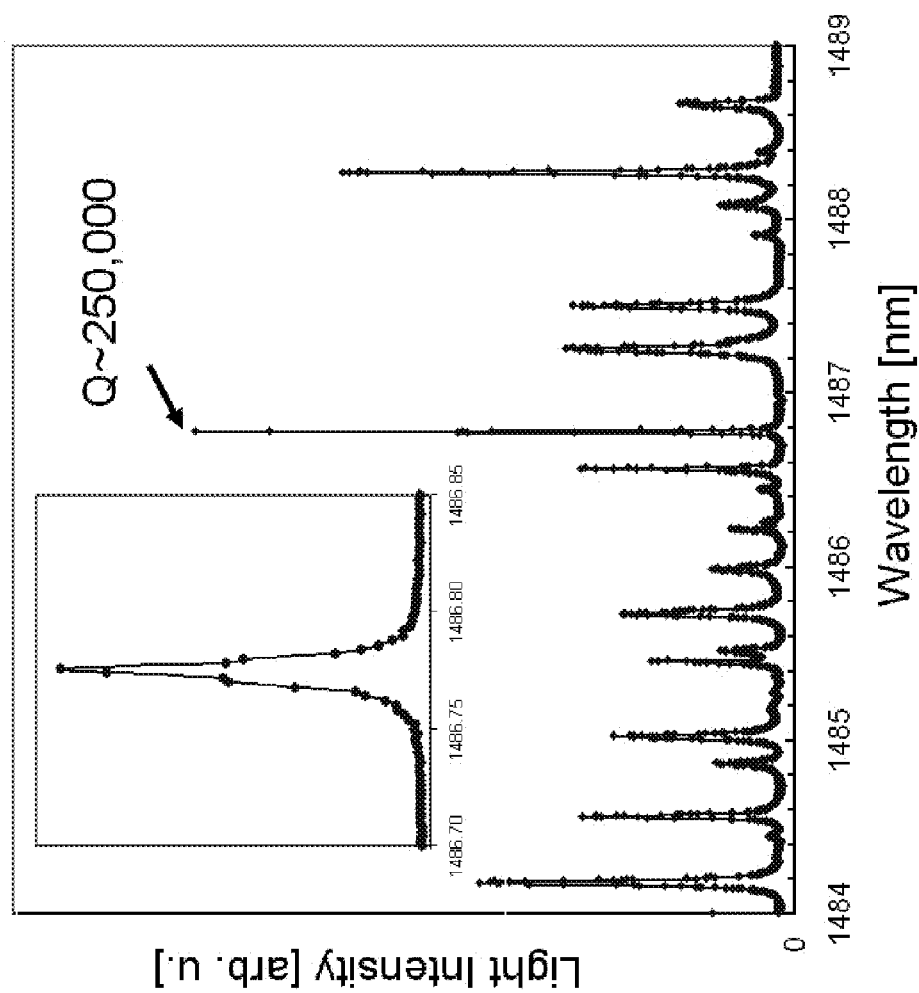
FIG. 13 is a detailed spectra collected from a weakly disordered PhC waveguide showing a high-Q localized mode. The modal volume was determined from far field images to less than 1 μm$^3$.

The data summarizing the effect of the disorder level on the quality of photon confinement is shown in FIGS. 12(a) and (b). Our measurements suggest that the spectral width of the localization band increases with disorder (FIG. 12(a)), the quality of photon confinement represented by the Q-factor decreases (FIG. 12(b)) with increasing amount of disorder. The largest Q-factor of ~250,000 was observed in circles disordered very weakly with e-beam deflection jitter. Portion of the spatially integrated scattered spectra with the high-Q mode is shown in FIG. 13. Inset of FIG. 13 illustrates a resonance with Q~250 000.

Figure 14A:
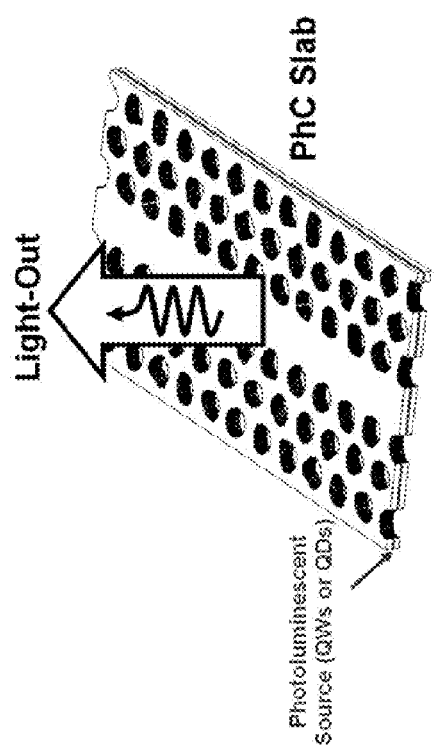
FIG. 14A illustrates a random laser of a preferred embodiment of the present invention. A disordered photonic crystal waveguide contains a gain medium or a photoluminescent source such as Quantum wells (QWs) or quantum dots (QDs) illustrated by embedded red layer. The QWs/QDs are pumped electrically or optically. Upon pumping, the structure emits light into the waveguide and out of the slab (light out).
Figure 14B:
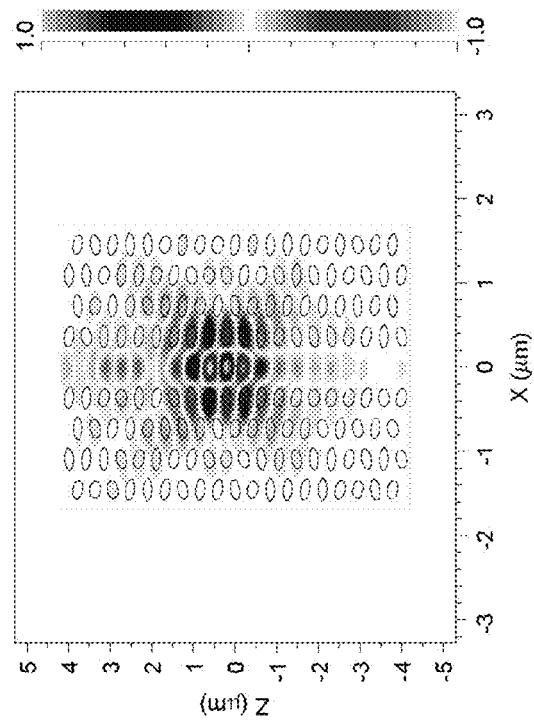
FIG. 14B illustrates a simulation of a mode confined in a disordered photonic crystal slab.
Figure 15:
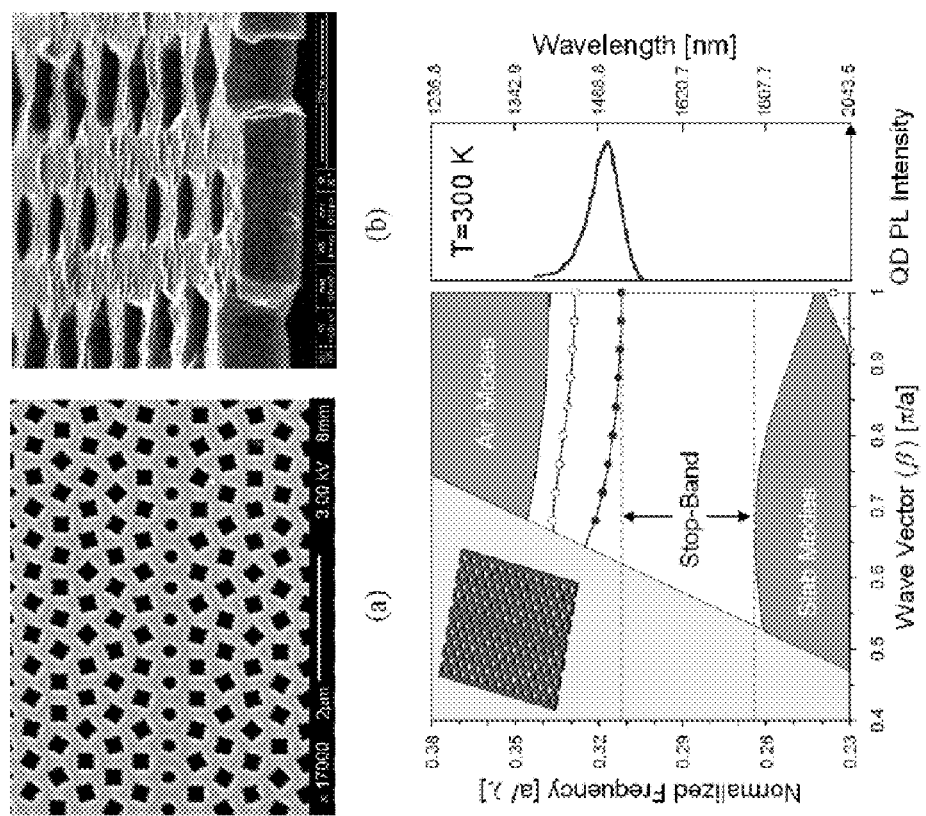
FIG. 15A is a scanning electron micrograph of the fabricated Si-based two-dimensional disordered photonic crystal waveguide.
FIG. 15B is a cross section of the photonic crystal showing polymer-dissolved PbSe quantum dots embedded into photonic crystal structure.
FIG. 15C is a graph of calculated dispersion of the defect waveguide in the ideal crystal shown in the inset (hollow circles denote odd modes and solid circles denote even modes). The photonluminescence spectra of the PbSe quantum dot (QD) shows that its emission peaks co-localized with the cut-off frequency of the disordered waveguide.
Figure 16:
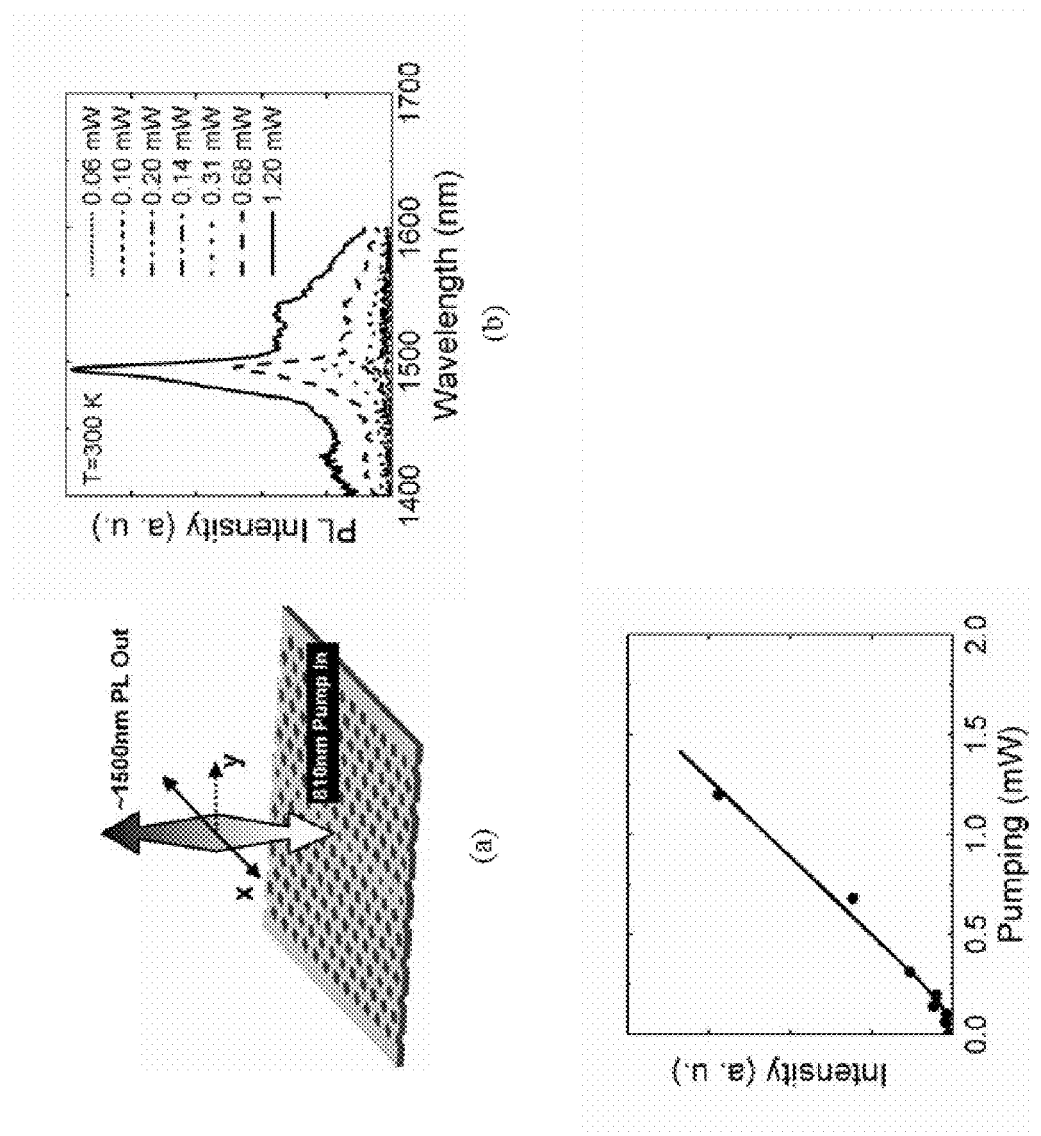
FIG. 16 (c) L-L characteristics of a silicon random photonic crystal microcavity with PbSe quantum dots measured at 300K at different pump powers.

Gain medium can be introduced in the photonic crystal waveguide slabs, e.g. using GaAs as substrate with embedded quantum dot (QD) in a so called heterostructure. See S. Chakraverty, P. Bhattacharya, S. Chakrabarti, Z. Mi, Opt. Lett. 32, 1296 (2007). FIG. 14A illustrates a disordered photonic crystal waveguide contains a gain medium or a photoluminescent source such as Quantum wells (QWs) or quantum dots (QDs) illustrated by embedded red layer. The QWs/QDs are pumped electrically or optically. Upon pumping, the structure emits light into the waveguide and out of the slab (light out). Disorder introduced in such an active, multi-layer structure (Quantum dots+slab substrate) can localize the emitted light in random-nano-laser devices. A simulation of a localized mode for random lasing in a disorderd structure is shown in FIG. 14B. The process of lasing in such a disordered structure is self-optimized since the highest-Q mode will suppress emission from lower-Q cavities. Active structures were fabricated by spin coating of colloidal quantum dots embedded in a suitable polymer on disordered photonic crystal slabs (FIG. 15). The evanescent field of randomly localized modes in the disordered waveguide structure excite the photoluminescence of the spin-coated colloidal quantum dots. To optimize this process, randomized W1 waveguides (FIG. 15A) were further modified with a row of non-randomized lattice elements located at the center of the waveguide (FIG. 15B). The additional lattice elements force the electromagnetic modes to more effectively overlap with QD deposited by spin coating on the PhC top surface and side-walls (see residue of spin coated polymer in FIG. 15B). To optimize excitation of QDs, their PL intensity is spectrally matched with the cutoff-frequency of the W1 waveguide mode in the near-infrared (FIG. 15C). Excitation of QDs (here using 810 nm pump laser focused from the top on the PhC slab, FIG. 16A) leads to light amplified stimulated emission of radiation (FIG. 16B) once the threshold for the pump power has been reached (FIG. 16C). Lasing is characterized by a narrowing of the linewidth of the enhanced photoluminescence peak (FIG. 16B and FIG. 16D). In general, the active photonic crystal slabs can be pumped with a focused, free space laser beam that excites the quantum dots or with an optical pump guided to the active region through waveguides.

Figure 17A:
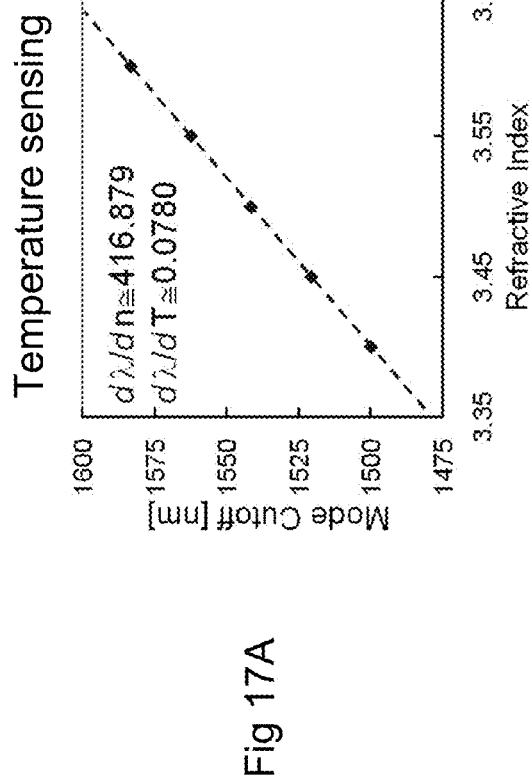
FIG. 17A is a calculated (dashed line) shift of a W1 waveguide band edge (mode cutoff) for changes in refractive index of the photonic crystal slab (hexagonal lattice, fill factor f=r/a=0.3, lattice constant a=410 nm, slab thickness=210 nm, refractive index of surrounding medium n=1.0) which can be induced by thermal tuning of the silicon slab (refractive index n~3.52 at room temperature). The thermo-optic tuning coefficient for wavelength shift is determined from the slobe of this plot as dλ/dT=0.0780 nm/K.
Figure 17B:
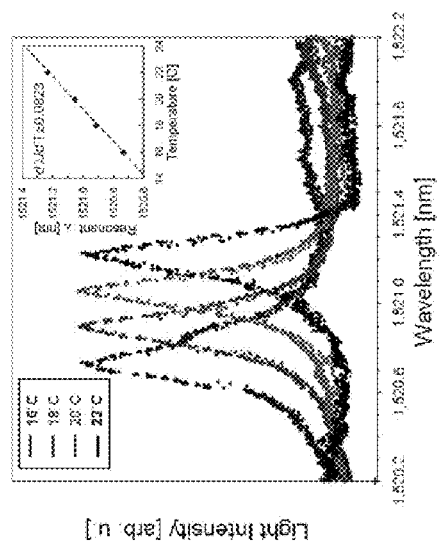
FIG. 17B shows Lorentzian shaped resonant lines for a preferred embodiment of the present invention. The resonance wavelength (determined from the maximum of the Lorentzian shaped resonant lines in FIG. 17B) is plotted versus temperature in the inset of FIG. 17B. Thermooptic tuning coefficient is measured at dλ/dT~0.0823 nm/K, consistent with the predictions from simulation (dλ/dT=0.0780 nm/K).

Disordered photonic crystal waveguides for sensing applications are describe in the following examples. For temperature sensing (FIG. 17), the scattering spectrum from the waveguide is acquired repeatedly over a limit frequency range over which the narrow spectral features due to random localization are observed (slow light regime of the waveguide). This can be done by either collecting the scattering spectra using an objective (as outlined before) or by using the light back-scattered through the fiber-taper that excites the waveguide (FIG. 2). For this purpose, a circulator or a fiber coupler can be used. The backscattered light is then collected through one of the fiber ports. Furthermore, a transmission spectrum of the waveguide can be collected with an objective aligned to the waveguide output or with another non-linear fiber taper aligned at the waveguide output (FIG. 2). Tuning of PhC slab temperature changes the refractive index, here of silicon by ~$1.8 \times 10^{-4}$ refractive index units/K (at 1.55 μm wavelength). Temperature tuning of refractive index off-sets the wavelength of the light localized in the disordered photonic crystal structure. Scattering/backscattering or transmission spectra taken at different temperatures therefore show a shift $\delta\lambda$ of the wavelength of a quasimode in the slow light regime (FIG. 17B). The shift is directly related to the change in refractive index and it is possible to measure the thermo-optic tuning coefficient $d\lambda/dT=0.0823$ nm/K (inset FIG. 15B), which agrees with theoretical predictions for the shift of the W1 mode cutoff calculated by plain wave expansion (FIG. 17A).

Figure 18A:
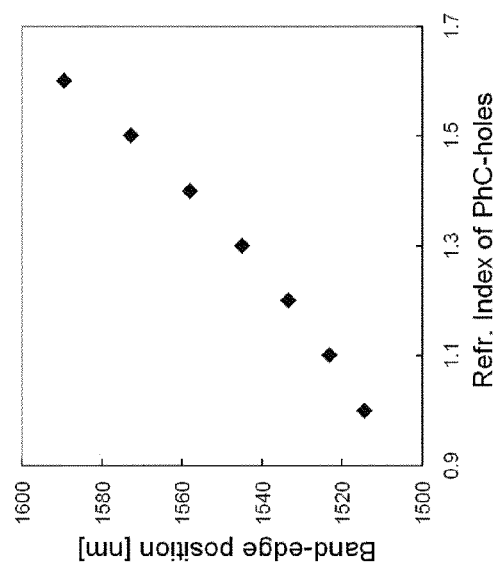
FIG. 18 illustrates calculated (A, plain wave expansion, W1 waveguide, hexagonal lattice, f=r/a=0.3, a=410 nm, slab thickness=210 nm, refractive index of slab n=3.52) and measured (B) wavelength shift of a W1 waveguide band edge for changes in refractive index of the medium surrounding the photonic crystal waveguide slab. Measurements (FIG. 18B) show resonant peaks (due to strong photon localization in the disordered W1 waveguide, dashed line) in air (refractive index n=1.0) and after the photonic crystal slab was immersed in 10% glycerol solution (refractive n=1.3475). The resonant peaks track the position of the band edge and shift with increase of the refractive index of the surrounding medium (~30 nm in 10% glycerol). The data illustrates use of disordered photonic crystal slabs as refractometric sensors.
Figure 18B:
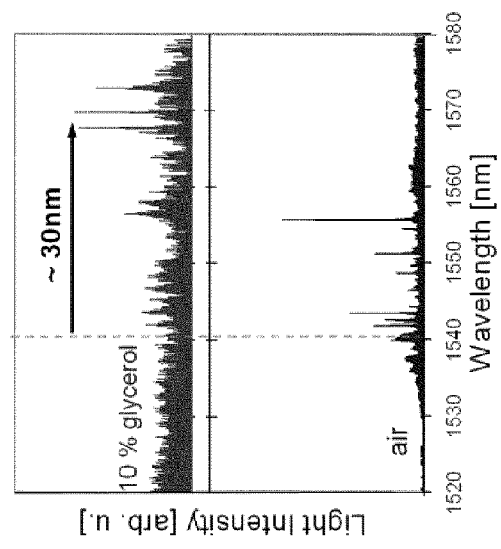

For refractive index sensing, the disordered photonic crystal waveguide is immersed in a liquid environment. This may be achieved by integration of the photonic crystal slab in a microfluidic channel. Alternatively, the channel defined by removal of the bottom SiO2 layer (FIG. 1C) may be used directly to deliver fluids to the disordered waveguide structure. By controlling the flow through the channel, the disordered waveguide may be exposed to liquids of different refractive index. Changes in refractive index of the environment of the photonic crystal (usually n=1 in air) will shift the position of the W1 waveguide mode edge as seen in calculation based on plain-wave expansion in FIG. 18A. Therefore, the wavelength $\delta\lambda$ of a quasimode changes for different refractive indexes of the medium surrounding the PhC. The measured shift of quasimodes (FIG. 18B) tracks the position of the W1 waveguide bandedge (FIG. 18A) as the refractive index of the surrounding medium is varied by immersing the PhC structure in 10% glycerole.

Figure 19:
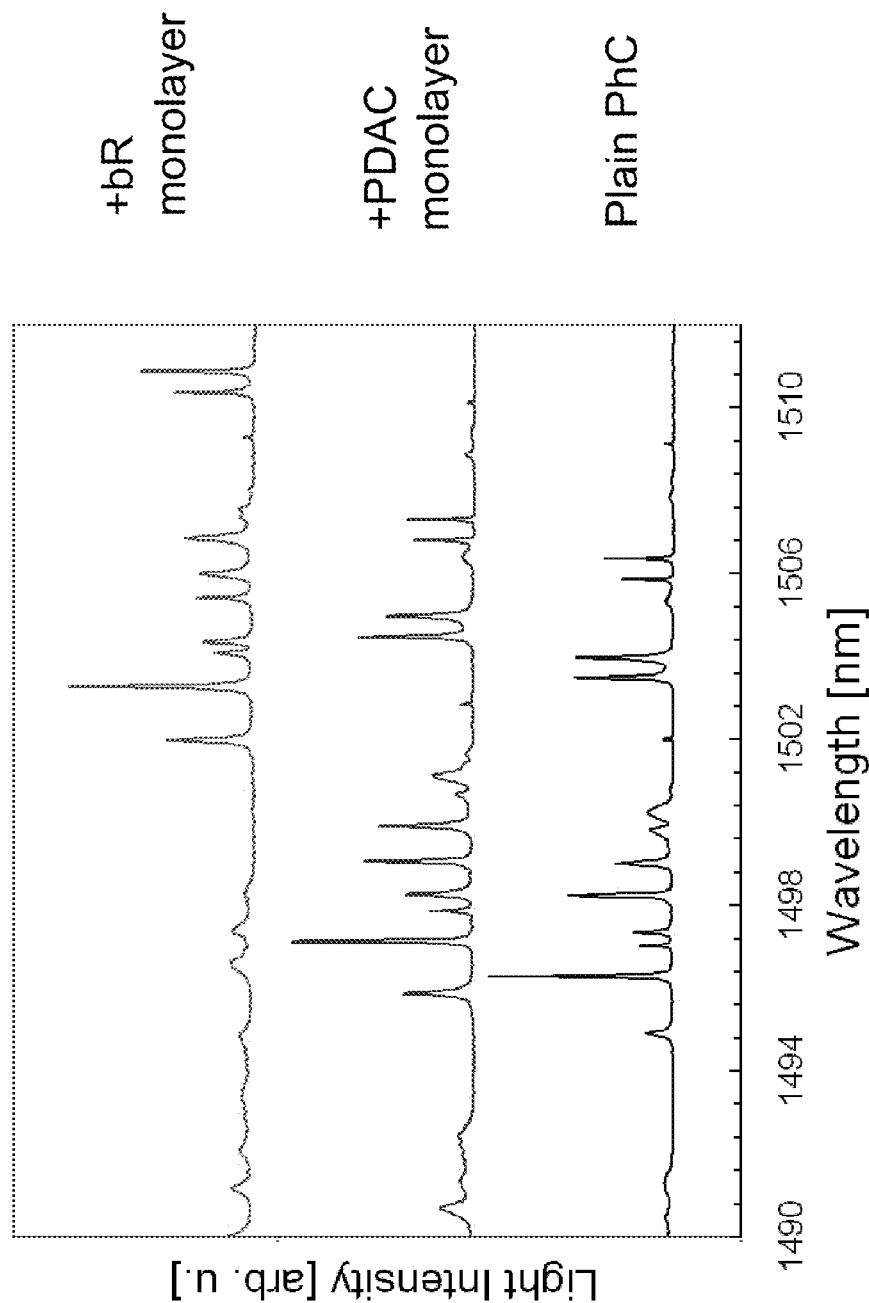
FIG. 19 shows the spectral features of a disordered photonic crystal waveguides without any adlayer (plain), after assembly of a poly(dimethyldiallyl)ammoniumchloride (PDAC) monolayer and after additional assembly of a bacteriorhodopsin (bR) monolayer on its top surface. For each added monolayer the spectral signatures shift to a longer wavelength.
Figure 20:
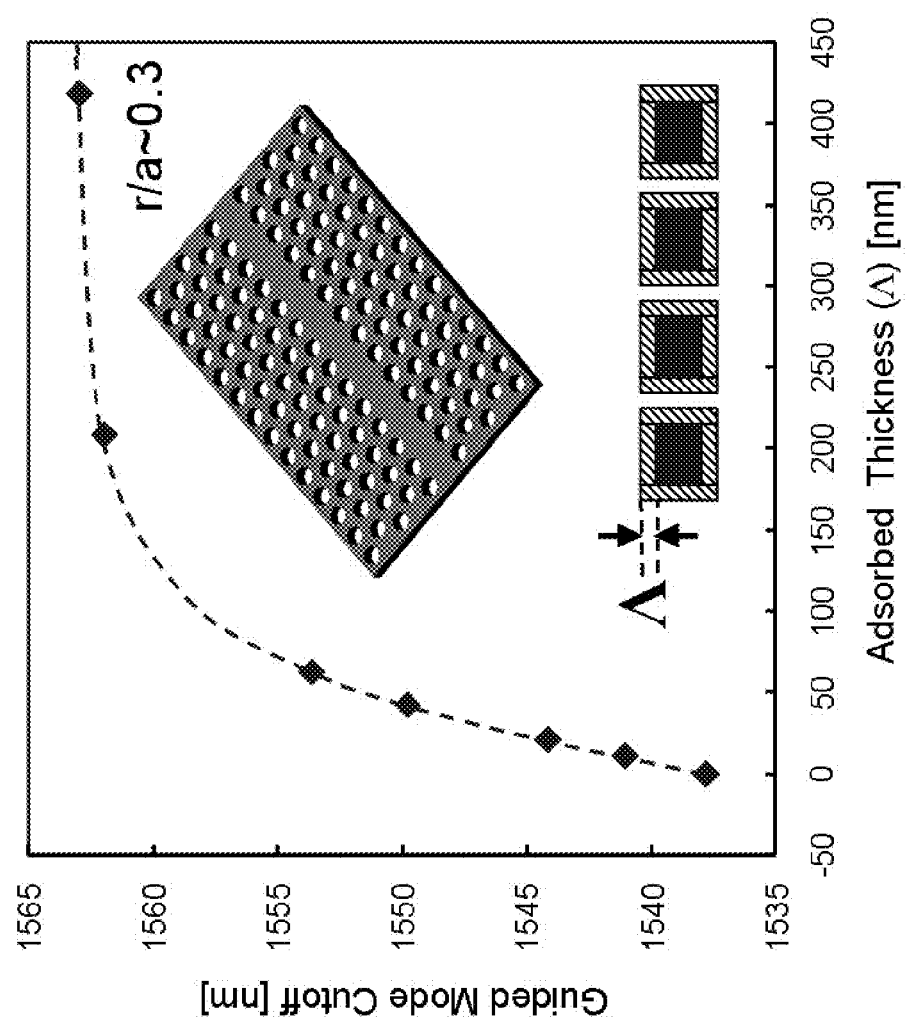
FIG. 20 illustrates calculated shift of a waveguide band edge for adsorption of an adlayer (thickness Λ) on the surface of the photonic crystal slab (plain wave expansion, W1 waveguide, hexagonal lattice, f=r/a=0.3, a=410 nm, slab thickness=210 nm, refractive index of slab n=3.52; refractive index of adlayer n=1.55; refractive index of surrounding medium n=1). Illustration in the inset shows that the adlayer covers bottom and upper surface as well as the sidewall of the PhC holes. The formation the adlayer can be monitored from shift of the resonant wavelength of a localized mode in the disordered photonic crystal slab which tracks the position of the cutoff wavelength (band edge).

The disordered photonic crystal waveguide may also be used for detection of molecules such as proteins, DNA or lipids. In one embodiment (FIG. 19), an adlayer of molecules (PDAC) is directly deposited on a surface of the disordered photonic crystal waveguide. This was achieved by exposing the structure to a liquid with dissolved PDAC molecules e.g. in a microfluidic channel. The specific binding of molecules to a surface or mode volume can be achieved by modification of the surface or the volume with a ligand. For example, an antibody may be adsorbed directly to the silicon surface. (Or the silicon surface as well as the volume of the holes defining the photonic crystal may be modified with a hydrogel such as dextran. The hydrogel may carry specific chemical linkers such as biotin or N-succinimylimide which allows for specific coupling to ligands such as antibodies (streptavidin- or amine modified)). Binding of the molecules creates an adlayer of thickness Λ with a refractive index higher than surrounding liquid medium. For the case of PDAC, the addition of a monolayer shifts the location of the quasimodes to longer wavelength (FIG. 19). In the calculation shown in FIG. 20, this shift of the band edge due to adsorption of an adlayer is modeled with different thickness and a refractive index of n=1.55. The shift is due to polarization of the added molecules at optical frequency. By tracking the shift of a resonance wavelength of a quasimode (which shifts proportional to change in cutoff wavelength) it is thus possible to monitor in real time the binding and unbinding of molecules. Tracking of the resonance wavelength of a quasimode can be achieved by acquiring a spectra with a computer, finding the maxima of a Lorentzian shaped peak that corresponds to a localized mode by polynomial fitting algorithm; recording the position of the maxima over time; plotting the position of the maxima versus time results in a binding curve. Alternatively, shift of a quasimode will change the intensity of transmitted/scattered light measured at a fixed frequency identical or close to the resonance frequency of a quasimode. Plain wave expansion can simulate the experiments and it is possible to determine either thickness or effective refractive index of the adsorbed layer from measurement of the wavelength shift or from measurements of changes in intensity at a fixed wavelength. If the experiment can be performed for several wavelength in parallel, thickness as well as refractive index of an adlayer can be determined from one measurement. If the experiment can be performed for several polarizations (or for several modes, even and odd) in parallel, it is possible to determine the orientation of a bound molecule (see PCT Application Serial No. PCT/US2007/68683 filed on May 10, 2007 naming Frank Vollmer and Juraj Topolancik as inventors and entitled "Methods, Materials and Devices for Light Manipulation with oriented Molecular Assemblies in Micronscale Photonic Circuit Elements with High-Q or Slow Light" and PCT Application Serial No. PCT/U.S.07/78586 entitled "Methods And Devices For Measurements Of Optical Anisotropy, Molecular Orientation And Polarizability Using Pump-Probe Spectroscopy In High-Q Microcavities" filed on 15, Sep. 2006 by Frank Vollmer and Juraj Topolancik.). Several adlayers may be assembled consecutively as shown for PDAC monolayer formation and subsequent bacteriorhodopsin (bR) monolayer formation (FIG. 19). Each adlayer shifts the spectral signature of quasimodes by a well-defined wavelength change.

Furthermore, a pump probe spectroscopy can be implemented where an optical pump centered at a molecular absorption band induces changes in molecular structure which are then monitored off-molecular resonance with, e.g., an infrared probe (here 1.55 μm wavelength). Details of this method are described in PCT Application Serial No. PCT/U.S.07/08683 by Frank Vollmer and Juraj Topolancik for "Methods, Materials and Devices for Light Manipulation with oriented Molecular Assemblies in Micronscale Photonic Circuit Elements with High-Q or Slow Light" filed on 11th May 2007.

In another embodiment, the disordered photonic crystal waveguide can be used to track changes in molecules structure. For example, G-protein coupled receptors respond to ligands and light by conformational changes. One example is the photochromic photoreceptor rhodopsin. In bacteriorhodopsin, structurally related to the visual rhodopsin, exposure to ~568 nm wavelength yellow light switches the molecular conformation of the chromophore retinal from all-trans to 13-cis. The reverse can be achieved by exposure to ~412 nm wavelength blue light. Bacteriorhodopsin self-assembles as a lipid-bilayer membrane on silicon surfaces. If Bacteriorhodpsin has been self-assembled on parts of the surface of a disordered photonic crystal waveguide, switching of its conformation using visible pumps (green/blue) can be monitored from shits of (even and odd) quasimodes excited in the near-infrared. By tracking the position of the near-infrared quasimode resonance wavelength it is possible to follow structural rearrangement of molecules in real time.

In another embodiment of our invention, the unique fingerprint of the resonance observed in scattering/backscattering or transmission through a disordered photonic crystal waveguide is used as a barcode label. The relative locations and amplitudes of the quasimodes can be exploited for identification of an object tagged with the micrometer-sized photonic crystal slab or for identification of the PhC slab itself.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An optical device comprising:
a slab, said slab comprising a material; and
a plurality of elements arranged in a lattice surrounding a photonic crystal waveguide, said lattice elements being formed in said slab by removing the material, with each said lattice element having a center located at a position (x,y), wherein first and second lattice elements differ in shape or orientation depending on their position (x,y) in the lattice, and said lattice is disordered due to randomized orientation of said lattice elements or geometrical perturbations introduced into said lattice elements, and wherein said lattice elements cause a localized guided light field of the waveguide; wherein said difference in the shape of said first and said second lattice elements is defined by a disorder function of permittivity $\Delta£(x,y)$ so that $\Delta£(x,y)=£_{real}(x,y)-£_{ideal}(x,y)$, where $£_{ideal}(x,y)$ represents the permittivity of an ideal lattice with perfect translational symmetry, (x,y) correspond to any position (point) in the lattice, $£_{real}(X,y)$ corresponds to the permittivity values at points (x,y).

2. The optical device according to claim 1, wherein area of said lattice elements, spacing of said lattice elements, symmetry of said lattice and arrangement of said lattice elements is chosen so that the device exhibits photonic band gap.

3. The optical device according to claim 1, wherein said slab material comprises one or more of the following: silicon, silicon nitride, Gallium-Arsenide, a metal, a semiconductor, a polymer, a composite material, quantum dots, quantum wells.

4. The optical device according to claim 1, wherein said lattice elements have been removed at lattice positions (x,y) so that a row of missing elements is formed along a certain crystallographic direction of the lattice.

5. The optical device according to claim 1, wherein said different shapes of the lattice elements comprise a circular shape where a radius r is parameterized as r(alpha,x,y), where alpha is an angle and (x,y) the position of the element in the lattice and r(alpha,x,y) is not a constant.

6. The optical device according to claim 1, wherein said lattice elements comprise polygons and wherein orientations of said polygons is varied by rotating a given polygon by an angle alpha(x,y) that varies with the lattice position (x,y).

7. The optical device according to claim 1, wherein said lattice elements comprise ellipses and wherein orientations of said ellipses is varied by rotating a major axis of a given ellipse by an angle alpha (x,y) that varies with the lattice position (x,y).

8. The optical device according to claim 1, wherein a number of said lattice elements is removed to define a defect cavity, an add-drop filter, a Mach-Zehnder interferometer, or a waveguide.

9. The optical device according to claim 1, wherein parts of the device surface are further modified by adding one of the following: photochromic molecules, protein, DNA, fluorophore, colloidal quantum dots, hydrogel, dextran, biotinylated polymers, antibodies, chelating ligands, biospecific recognition elements.

10. The optical device according to claim 1, wherein said slab material further contains optical gain material such as wherein said optical gain material comprises at least one of quantum dots, quantum wells, one or more layers of quantum dots grown by molecular beam epitaxy, and one or more layers of quantum wells grown by molecular beam epitaxy.

11. The optical device according to claim 1, wherein a tapered optical fiber tip is used to evanescently couple light to one or more lattice positions (x,y) where said lattice elements have been removed.

12. The optical device according to claim 1 that is exposed to a sample comprising one of the following: a solution, a gas, an aerosol, protein, DNA, viral particles, cells, body fluids.

13. The optical device according to claim 1 comprising a barcode label reader comprising the steps of:
measuring a scattering or transmission spectrum using a laser; recording said transmission spectrum on a computer; matching the spectrum to a database using computer algorithms.

14. A method for measurements of spectral features comprising the steps of:
excitation of an optical device using a tunable laser, said optical device comprising a slab, said slab comprising a material and a plurality of elements arranged in a lattice surrounding a photonic crystal waveguide, said lattice elements being formed in said slab by removing the material, with each said lattice element having a center located at a position (x,y), wherein first and second lattice elements differ in shape or orientation depending on their position (x,y) in the lattice and said difference in the shape of said first and said second lattice elements is defined by a disorder function of permittivity $\Delta\epsilon(x,y)$ so that $\Delta\epsilon(x,y)=\epsilon_{real}(x,y)-\epsilon_{ideal}(x,y)$, where $\epsilon_{ideal}(x,y)$ represents the permittivity of an ideal lattice with perfect translational symmetry, (x,y) correspond to any position (point) in the lattice, $\epsilon_{real}(X,y)$ corresponds to the permittivity values at points (x,y), and said lattice is disordered due to randomized orientation of said lattice elements or geometrical perturbations introduced into said lattice elements, wherein said randomize orientation of said lattice elements or said geometrical perturbations introduced into said lattice elements produce localized mode devices in said photonic crystal waveguide;
detection of transmission or scattering or backscattering spectra using a photodetector; and
analysis of a recorded spectrum using a computer.

15. A method for tracking changes in spectral features of a optical device, said optical device comprising a slab, said slab comprising a material and a plurality of elements arranged in a lattice surrounding a photonic crystal waveguide, said lattice elements being formed in said slab by removing the material, with each said lattice element having a center located at a position (x,y), wherein first and second lattice elements differ in shape or orientation depending on their position (x,y) in the lattice and said difference in the shape of said first and said second lattice elements is defined by a disorder function of permittivity $\Delta\epsilon(x,y)$ so that $\Delta\epsilon(x,y)=\epsilon_{real}(x,y)-\epsilon_{ideal}(x,y)$, where $\epsilon_{ideal}(x,y)$ represents the permittivity of an ideal lattice with perfect translational symmetry, (x,y) correspond to any position (point) in the lattice, $\epsilon_{real}(X,y)$ corresponds to the permittivity values at points (x,y), and said lattice is disordered due to randomized orientation of said lattice elements or geometrical perturbations introduced into said lattice elements, wherein said randomize orientation of said lattice elements or said geometrical perturbations introduced into said lattice elements produce localized mode devices in said photonic crystal waveguide, comprising the steps of:
identifying a wavelength associated with a minima or maxima in a recorded spectral feature using computer algorithms;
recording the wavelengths of said minima or maxima over time; and plotting a time trace of said recorded wavelengths for further analysis with a computer.

16. A method for tracking changes in spectral features of a device, said device comprising a slab, said slab comprising a material and a plurality of elements arranged in a lattice surrounding a photonic crystal waveguide, said lattice elements being formed in said slab by removing the material, with each said lattice element having a center located at a position (x,y), wherein first and second lattice elements differ in shape or orientation depending on their position (x,y) in the lattice and said difference in the shape of said first and said second lattice elements is defined by a disorder function of permittivity $\Delta\epsilon(x,y)$ so that $\Delta\epsilon(x,y)=\epsilon_{real}(x,y)-\epsilon_{ideal}(x,y)$, where $\epsilon_{ideal}(x,y)$ represents the permittivity of an ideal lattice with perfect translational symmetry, (x,y) correspond to any position (point) in the lattice, $\epsilon_{real}(X,y)$ corresponds to the permittivity values at points (x,y) and said lattice is disordered due to randomized orientation of said lattice elements or geometrical perturbations introduced into said lattice elements, wherein said randomize orientation of said lattice elements or said geometrical perturbations introduced into said lattice elements produce localized mode devices in said photonic crystal waveguide, comprising the steps of:
recording spectral features before exposure to a sample; exposing said device to said sample; recording spectral features during and after sample exposure; and
analyzing changes in spectral features using computer algorithms.

17. The method for tracking changes in spectral features of a device according to claim 16, wherein said step of exposing said device to the sample comprises the steps of:
sample delivery by microfluidic flow, electrophoretic flow, aerosol flow or by electrowetting;
exposure of said device to said sample for a certain time period; and
removing of said sample by exposing said optical device to a second microfluidic or electrophoretic flow.

* * * * *